United States Patent [19]
Nesvadba et al.

[11] Patent Number: 5,932,642
[45] Date of Patent: Aug. 3, 1999

[54] CYCLIC PHOSPHINIC ACID DERIVATIVES AS STABILIZERS

[75] Inventors: Peter Nesvadba, Marly; Paul Dubs, Fribourg, both of Switzerland

[73] Assignee: Ciba Specialty Chemicals Corporation, Tarrytown, N.Y.

[21] Appl. No.: 08/994,976

[22] Filed: Dec. 19, 1997

[30] Foreign Application Priority Data

Dec. 24, 1996 [CH] Switzerland .............................. 3198/96

[51] Int. Cl.⁶ ........................ C08K 5/5393; C07F 9/6574
[52] U.S. Cl. ............................ 524/117; 524/119; 558/76; 558/82
[58] Field of Search ................................... 524/117, 119; 558/76, 82

[56] References Cited

U.S. PATENT DOCUMENTS

| | | |
|---|---|---|
| 3,029,276 | 4/1962 | Hausweiler et al. . |
| 3,702,878 | 11/1972 | Saito . |
| 4,276,232 | 6/1981 | Rasberger . |
| 4,325,863 | 4/1982 | Hinshen et al . |
| 4,388,244 | 6/1983 | Carlos . |
| 5,175,312 | 12/1992 | Dulis et al. . |
| 5,216,052 | 6/1993 | Nesvadba et al. . |
| 5,252,643 | 10/1993 | Nesvadba . |
| 5,414,033 | 5/1995 | Nesvadba . |
| 5,650,530 | 7/1997 | Buysch et al. . |

FOREIGN PATENT DOCUMENTS

| | | |
|---|---|---|
| 352 | 6/1978 | European Pat. Off. . |
| 589839 | 9/1993 | European Pat. Off. . |
| 591102 | 9/1993 | European Pat. Off. . |
| 705870 | 3/1995 | European Pat. Off. . |
| 703241 | 9/1995 | European Pat. Off. . |
| 0 748 811 | 12/1996 | European Pat. Off. . |
| 4316611 | 11/1993 | Germany . |
| 4316622 | 11/1993 | Germany . |
| 4316876 | 11/1993 | Germany . |
| 1082273 | 5/1960 | Switzerland . |

OTHER PUBLICATIONS

File Registry on STN®, Chemical Abstracts Service, (Columbus, Ohio), File CA Accession No. 126:89571; Regnat et al. EP 0 748 811, Dec. 18, 1996, abstract. 1997.

R. Gachter/ H. Muller (Ed.) Plastics Additives Handbook 3$^{rd}$ Ed., pp. 47–104 Hanser, Munchen 1990.

Ullmann's Encyklopaie der technischen Chemie, vol. 13, pp. 85–94 (Verlag Chemie, Weihiem).

Chemical Abstract 97 (20): 164043, (1982).

A. Nishinaga, et al. J. Organic Chemistry 51 (12) 2257–2266 (1986).

G. Casiraghi, et al., Synthesis 1977, 122–124.

*Primary Examiner*—Michael G Ambrose
*Attorney, Agent, or Firm*—Luther A. R. Hall

[57] ABSTRACT

A description is given of novel compounds of formula I

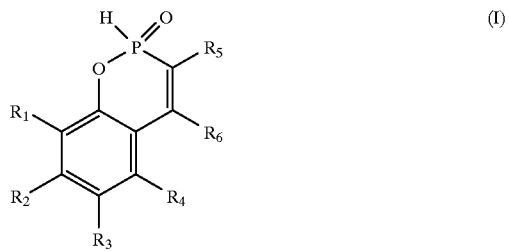

wherein $R^1$, $R_2$, $R_3$, and $R^4$ are hydrogen, alkyl, phenylalkyl, or alkoxy and where $R_5$ and $R_6$ are hydrogen or phenyl or together with the linking carbon atoms, are cycloalkenylene or cycloalkenylene which is interrupted by oxygen or sulfur. These compounds are useful as stabilizers for organic materials against oxidative, thermal or light-induced degradation.

19 Claims, No Drawings

CYCLIC PHOSPHINIC ACID DERIVATIVES AS STABILIZERS

The present invention relates to novel cyclic phosphinic acid derivatives, to compositions comprising an organic material, preferably a polymer, and the novel cyclic phosphinic acid derivatives, as well as to the use thereof for stabilising organic materials against oxidative, thermal or light-induced degradation.

Organic phosphites, phosphonites and phosphorus amides are known in the art as costabilisers, secondary antioxidants and processing stabilisers used, inter alia, for polyolefins. Examples of such known phosphite stabilisers are to be found in R. Gächter/H. Müller (Ed.), Plastics Additives Handbook, 3rd Ed., page 47, Hanser, München 1990.

U.S. Pat. No. 3,702,878 discloses novel organophosphorus compounds and processes for their preparation.

The known stabilisers do not in every respect meet the high demands that a stabiliser should fulfill, in particular as regards storage stability, absorption of water, susceptibility to hydrolysis, processing stabilisation, colour behaviour, volatility, migration behaviour, compatibility and enhancement of light stability. There is therefore still a need for effective stabilisers for organic materials which are susceptible to oxidative, thermal and/or light-induced degradation.

It has now been found that a novel chemical process makes it possible to prepare novel cyclic phosphinic acid derivatives which are particularly suitable as stabilisers for organic materials susceptible to oxidative, thermal or light-induced degradation. To be highlighted in particular is the suitability of the cited compounds as processing stabilisers for synthetic polymers.

Accordingly, this invention relates to compounds of formula I

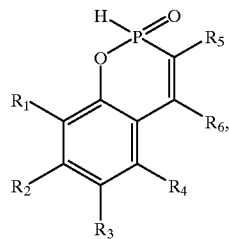

(I)

wherein $R_1$, $R_2$, $R_3$ and $R_4$ are each independently of one another hydrogen, halogen, hydroxy, $C_1$–$C_{25}$alkyl; $C_2$–$C_{25}$alkyl which is interrupted by oxygen, sulfur or

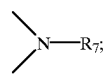

$C_2$–$C_{24}$alkenyl, $C_7$–$C_9$phenylalkyl, unsubstituted or $C_1$–$C_4$alkyl-substituted phenyl; unsubstituted or $C_1$–$C_4$alkyl-substituted $C_5$–$C_{12}$cycloalkyl; unsubstituted or $C_1$–$C_4$alkyl-substituted $C_5$–$C_{12}$cycloalkenyl; $C_1$–$C_{18}$alkoxy, $C_2$–$C_{24}$alkenyloxy, $C_1$–$C_{18}$alkylthio, $C_1$–$C_4$alkylamino, di($C_1$–$C_4$alkyl)amino, $C_1$–$C_{25}$alkanoyloxy, $C_1$–$C_{25}$alkanoylamino, $C_3$–$C_{25}$alkenoyloxy; $C_3$–$C_{25}$alkanoyloxy which is interrupted by oxygen, sulfur or

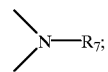

$C_5$–$C_9$cycloalkylcarbonyloxy, benzoyloxy or $C_1$–$C_{12}$alkyl-substituted benzoyloxy; or $R_1$ and $R_2$, or $R_2$ and $R_3$, or $R_3$ and $R_4$, together with the linking carbon atoms, form a benzene ring, $R_3$ additionally being —$(CH_2)_m$—$COR_8$ or —$(CH_2)_n OR_9$, or, if $R_2$ and $R_4$ are hydrogen, $R_3$ additionally being a radical of formula IIa, IIb or IIc

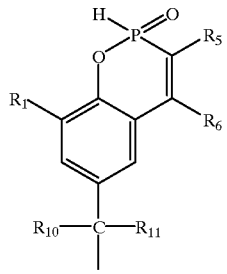

(IIa)

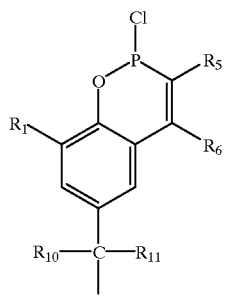

(IIb)

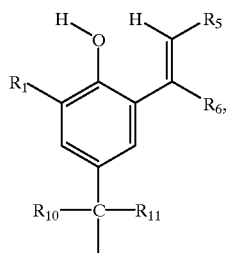

(IIc)

$R_5$ and $R_6$ are each independently of the other hydrogen, $C_1$–$C_{25}$alkyl; $C_2$–$C_{25}$alkyl which is interrupted by oxygen, sulfur or

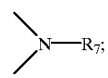

$C_7$–$C_9$phenylalkyl, unsubstituted or $C_1$–$C_4$alkyl-substituted phenyl; unsubstituted or $C_1$–$C_4$alkyl-substituted $C_5$–$C_{12}$cycloalkyl, or $R_5$ and $R_6$, together with the linking carbon atoms, are unsubstituted $C_5$–$C_{12}$cycloalkenylene or unsubstituted $C_4$–$C_{11}$cycloalkenylene which is interrupted by oxygen, sulfur or

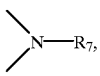

the rings of which are unsubstituted or substituted by $C_1$–$C_4$alkyl, by unsubstituted or $C_1$–$C_4$alkyl-substituted $C_5$–$C_{12}$cycloalkyl; by unsubstituted or $C_1$–$C_4$alkyl-substituted phenyl; or by unsubstituted or $C_1$–$C_4$alkyl-substituted phenylene, $R_7$ is hydrogen, $C_1$–$C_8$alkyl, $C_1$–$C_8$alkoxy, $C_1$–$C_8$alkanoyl or unsubstituted or $C_1$–$C_4$alkyl-substituted benzoyl, $R_8$ is hydroxy,

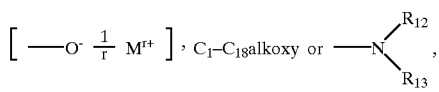

$R_9$ is hydrogen, $C_1$–$C_8$alkanoyl or unsubstituted or $C_1$–$C_4$alkyl-substituted benzoyl, $R_{10}$ and $R_{11}$ are each independently of the other hydrogen, $CF_3$, $C_1$–$C_{12}$alkyl, unsubstituted or $C_1$–$C_4$alkyl-substituted phenyl; or —$(CH_2)_s$—$COR_{14}$, or $R_{10}$ and $R_{11}$, together with the linking carbon atom, are a $C_5$–$C_{12}$cycloalkylidene ring which is unsubstituted or substituted by 1 to 3 $C_1$–$C_4$alkyl, $R_{12}$ and $R_{13}$ are each independently of the other hydrogen or $C_1$–$C_{18}$alkyl, $R_{14}$ is hydroxy, $C_1$–$C_{18}$alkoxy or

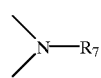

M is an r-valent metal cation,
m is 0, 1 or 2,
n is 1, 2, 3, 4, 5 or 6,
r is 1, 2 or 3, and
s is 0 or 1.

The compounds of formula I can also be obtained in a tautomeric form such as that of formula Ia

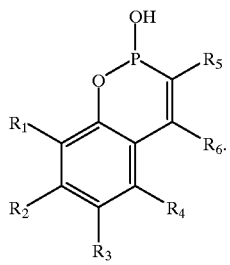

(Ia)

This invention of course also embraces the tautomeric structure of formula Ia of the structures given for the compounds of formula I.

Halogen is typically chloro, bromo or iodo. Chloro is preferred.

Alkyl of up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. One of the preferred meanings of R, $R_2$, $R_3$ and $R_4$ is, for example, $C_1$–$C_{18}$alkyl, in particular $C_1$–$C_{12}$alkyl, e.g. $C_1$–$C_{10}$alkyl. A particularly preferred meaning of $R_1$, $R_2$, $R_3$ and $R_4$ is $C_1$–$C_8$alkyl, in particular $C_1$–$C_6$alkyl, e.g. $C_1$–$C_4$alkyl. A preferred meaning of $R_5$ and $R_6$ is $C_1$–$C_{18}$alkyl, in particular $C_1$–$C_{12}$alkyl, e.g. $C_1$–$C_{10}$alkyl. A particularly preferred meaning of $R_5$ and $R_6$ is $C_1$–$C_8$alkyl, in particular $C_1$–$C_6$alkyl, e.g. $C_1$–$C_4$alkyl such as methyl. A preferred meaning of $R_7$ is $C_1$–$C_6$alkyl, in particular $C_1$–$C_4$alkyl, e.g. methyl, ethyl or n-propyl. A preferred meaning of $R_{10}$ and $R_{11}$ is $C_1$–$C_{10}$alkyl, in particular $C_1$–$C_8$alkyl, e.g. $C_1$–$C_6$alkyl. A particularly preferred meaning of $R_{10}$ and $R_{11}$ is $C_1$–$C_4$alkyl, in particular $C_1$–$C_3$alkyl, e.g. methyl. A preferred meaning of $R_{12}$ and $R_{13}$ is $C_1$–$C_{12}$alkyl, in particular $C_1$–$C_{10}$alkyl, e.g. $C_1$–$C_8$alkyl. A particularly preferred meaning of $R_{12}$ and $R_{13}$ is $C_1$–$C_6$alkyl, in particular $C_1$–$C_4$alkyl, e.g. methyl or ethyl.

$C_2$–$C_{25}$Alkyl which is interrupted by oxygen, sulfur or

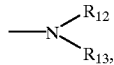

is a branched or unbranched radical such as $CH_3$—O—$CH_2$—, $CH_3$—S—$CH_2$—, $CH_3$—NH—$H_2$—, $CH_3$—N($CH_3$)—$CH_2$—, $CH_3$—O—$CH_2CH_2$—O—$CH_2$—, $CH_3$—(O—$CH_2CH_2$—)$_2$O—$CH_2$—, $CH_3$—(O—$CH_2CH_2$—)$_3$O—$CH_2$— or $CH_3$—(O—$CH_2CH_2$—)$_4$O—$CH_2$—.

Alkenyl of 3 to 24 carbon atoms is a branched or unbranched radical, for example vinyl, propenyl, 2-butenyl, 3-butenyl, isobutenyl, n-2,4-pentadienyl, 3-methyl-2-butenyl, n-2-octenyl, n-2-dodecenyl, isododecenyl, oleyl, n-2-octadecenyl or n-4-octadecenyl. It is preferred to use alkenyl of 2 to 18, preferably of 2 to 12, e.g. of 2 to 6, most preferably of 2 to 4, carbon atoms.

$C_7$–$C_9$Phenylalkyl is typically benzyl, α-methylbenzyl, α,α-dimethylbenzyl or 2-phenylethyl. Benzyl and α,α-dimethylbenzyl are preferred.

$C_1$–$C_4$Alkyl-substituted phenyl, which preferably carries 1 to 3, in particular 1 or 2, alkyl groups, is typically o-, m- or p-methylphenyl, 2,3-dimethylphenyl, 2,4-dimethylphenyl, 2,5-di-methylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Unsubstituted or $C_1$–$C_4$alkyl-substituted $C_5$–$C_{12}$cycloalkyl is typically cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl, cyclooctyl, cyclononyl, cyclodecyl, cycloundecyl or cyclododecyl. It is preferred to use unsubstituted or $C_1$–$C_4$alkyl-substituted $C_5$–$C_8$cycloalkyl, in particular $C_5$–$C_7$cycloalkyl, e.g. cyclohexyl and tert-butylcyclohexyl.

Unsubstituted or $C_1$–$C_4$alkyl-substituted $C_5$–$C_{12}$cycloalkenyl is, for example, cyclopentenyl, methylcyclopentenyl, dimethylcyclopentenyl, cyclohexenyl, methylcyclohexenyl, dimethylcyclohexenyl, trimethylcyclohexenyl, tert-butylcyclohexenyl, cycloheptenyl, cyclooctenyl, cyclononenyl, cyclodecenyl, cycloundecenyl or cyclododecenyl. It is preferred to use unsubstituted or $C_1$–$C_4$alkyl-substituted $C_5$–$C_8$cycloalkenyl, in particular $C_5$–$C_7$cycloalkenyl, e.g. cyclohexen1-yl and tert-butylcyclohexen-1-yl.

Alkoxy of up to 18 carbon atoms is a branched or unbranched radical, such as methoxy, ethoxy, propoxy, isopropoxy, n-butoxy, isobutoxy, pentoxy, isopentoxy, hexoxy, heptoxy, octoxy, decyloxy, tetradecyloxy, hexadecyloxy or octadecyloxy. It is preferred to use alkoxy of 1 to 12, in particular of 1 to 8, e.g. of I to 6, carbon atoms. A particularly preferred meaning of $R_1$, $R_2$, $R_3$, $R_4$, $R_7$, $R_8$ and $R_{14}$ is $C_1$–$C_4$alkoxy, in particular $C_1$–$C_3$alkoxy, e.g. methoxy or ethoxy.

Alkenyloxy of 2 to 25 carbon atoms is a branched or unbranched radical, for example vinyloxy, propenyloxy, 2-butenyloxy, 3-butenyloxy, isobutenyloxy, n-2,4-pentadienyloxy, 3-methyl-2-butenyloxy, n-2-octenyloxy, n-2-dodecenyloxy, isododecenyloxy, oleyloxy, n-2-octadecenyloxy or n-4-octadecenyloxy. It is preferred to use alkenyloxy of 3 to 18, in particular of 3 to 12, e.g. of 3 to 6, most preferably of 3 to 4, carbon atoms.

Alkylthio of up to 18 carbon atoms is a branched or unbranched radical, typically methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio. It is preferred to use alkylthio of 1 to 12, in particular of 1 to 8, e.g. of 1 to 6, carbon atoms.

Alkylamino of up to 4 carbon atoms is a branched or unbranched radical, such as methylamino, ethylamino, propylamino, isopropylamino, n-butylamino, isobutylamino or tert-butylamino.

Di($C_1$–$C_4$alkyl)amino also means that the two radicals are each independently of the other branched or unbranched, such as dimethylamino, methylethylamino, diethylamino, methyl-n-propylamino, methylisopropylamino, methyl-n-butylamino, methylisobutylamino, ethylisopropylamino, ethyl-n-butylamino, ethylisobutylamino, ethyl-tert-butylamino, diethylamino, diisopropylamino, isopropyl-n-butylamino, isopropylisobutylamino, di-n-butylamino or di-isobutylamino.

Alkanoyloxy of up to 25 carbon atoms is a branched or unbranched radical, for example formyloxy, acetoxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, eicosanoyloxy or docosanoyloxy. It is preferred to use alkanoyloxy of 2 to 18, in particular of 2 to 12, e.g. of 2 to 6, carbon atoms. Acetoxy is particularly preferred.

Alkanoylamino of up to 25 carbon atoms is a branched or unbranched radical, typically formylamino, acetylamino, propionylamino, butanoylamino, pentanoylamino, hexanoylamino, heptanoylamino, octanoylamino, nonanoylamino, decanoylamino, undecanoylamino, dodecanoylamino, tridecanoylamino, tetradecanoylamino, pentadecanoylamino, hexadecanoylamino, heptadecanoylamino, octadecanoylamino, eicosanoylamino or docosanoylamino. It is preferred to use alkanoylamino of 2 to 18, in particular of 2 to 12, e.g. of 2 to 6, carbon atoms.

Alkenoyloxy of 3 to 25 carbon atoms is a branched or unbranched radical, for example propenyloxy, 2-butenoyloxy, 3-butenoyloxy, isobutenoyloxy, n-2,4-pentadienoyloxy, 3-methyl-2-butenoyloxy, n-2-octenoyloxy, n-2-dodecenoyloxy, isododecenoyloxy, oleoyloxy, n-2-octadecenoyloxy or n-4-octadecenoyloxy. It is preferred to use alkenoyloxy of 3 to 18, in particular of 3 to 12, e.g. of 3 to 6, most preferably of 3 to 4, carbon atoms.

$C_3$–$C_{25}$Alkanoyloxy which is interrupted by oxygen, sulfur or

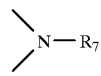

is, for example, $CH_3$—O—$CH_2$COO—, $CH_3$—S—$CH_2$COO—, $CH_3$—NH—$CH_2$COO—, $CH_3$—N($CH_3$)—$CH_2$COO—, $CH_3$—O—$CH_2CH_2$—O—$CH_2$COO—, $CH_3$—(O—$CH_2CH_2$—)$_2$O—$CH_2$COO—, $CH_3$—(O—$CH_2CH_2$—)$_3$O—$CH_2$COO— or $CH_3$—(O—$CH_2CH_2$—)$_4$O—$CH_2$COO—.

$C_5$–$C_9$Cycloalkylcarbonyloxy is typically cyclopentylcarbonyloxy, cyclohexylcarbonyloxy, cycloheptylcarbonyloxy, cyclooctylcarbonyloxy or cyclononylcarbonyloxy. Cyclohexylcarbonyloxy is preferred.

$C_1$–$C_{12}$Alkyl-substituted benzoyloxy, which preferably carries 1 to 3, in particular 1 or 2, alkyl groups, is typically o-, m- or p-methylbenzoyloxy, 2,3-dimethylbenzoyloxy, 2,4-dimethylbenzoyloxy, 2,5-dimethylbenzoyloxy, 2,6-dimethylbenzoyloxy, 3,4-dimethylbenzoyloxy, 3,5-dimethylbenzoyloxy, 2-methyl-6-ethylbenzoyloxy, 4-tert-butylbenzoyloxy, 2-ethylbenzoyloxy, 2,4,6-trimethylbenzoyloxy, 2,6-dimethyl-4-tert-butylbenzoyloxy or 3,5-di-tert-butylbenzoyloxy. Preferred substituents are $C_1$–$C_8$alkyl, in particular $C_1$–$C_4$alkyl.

If $R_5$ and $R_6$, together with the linking carbon atoms, are unsubstituted $C_5$–$C_{12}$cycloalkenylene, the ring of which is unsubstituted or substituted by $C_1$–$C_4$alkyl, by unsubstituted or $C_1$–$C_4$alkyl-substituted $C_5$–$C_{12}$cycloalkyl; by unsubstituted or $C_1$–$C_4$alkyl-substituted phenyl; or by unsubstituted or $C_1$–$C_4$alkyl-substituted phenylene, then this is typically cyclopentenylene, cyclohexenylene, cycloheptenylene, cyclooctenylene, cyclononenylene, cyclodecenylene, cycloundecenylene, cyclododecenylene, methylcyclopentenylene, methylcyclohexenylene, methylcycloheptenylene, methylcyclooctenylene, methylcyclononenylene, methylcyclodecenylene, methylcycloundecenylene, methylcyclododecenylene, trimethylcyclopentenylene, trimethylcyclohexenylene, trimethylcycloheptenylene, trimethylcyclooctenylene, trimethylcyclononenylene, trimethylcyclodecenylene, trimethylcycloundecenylene, trimethylcyclododecenylene, cyclohexylcyclopentenylene, cyclohexylcyclohexenylene, cyclohexylcycloheptenylene, cyclohexylcyclooctenylene, cyclohexylcyclononenylene, cyclohexylcyclodecenylene, cyclohexylcycloundecenylene, cyclohexylcyclododecenylene, phenylcyclopentenylene, phenylcyclohexenylene, phenylcycloheptenylene, phenylcyclooctenylene, phenylcyclononenylene, phenylcyclodecenylene, phenylcycloundecenylene, phenylcyclododecenylene,

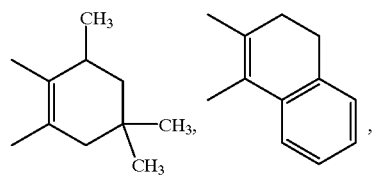

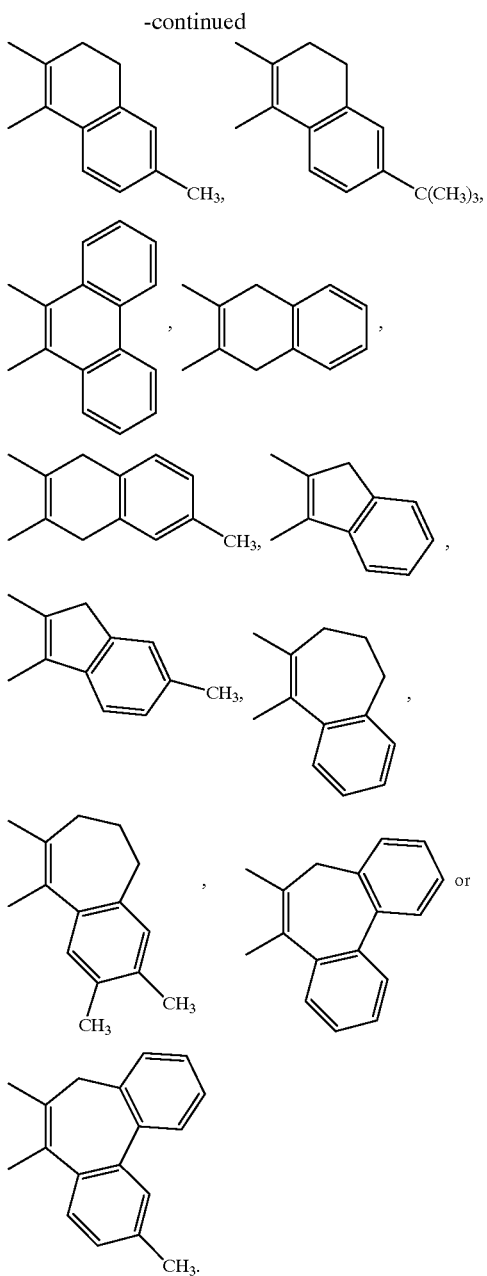

Together with the linking carbon atoms, $R_5$ and $R_6$ preferably are unsubstituted $C_5$–$C_9$cycloalkenylene, in particular $C_5$–$C_8$cycloalkenylene, e.g. $C_5$–$C_7$cycloalkenylene, the ring of which is unsubstituted or substituted by $C_1$–$C_4$alkyl, by unsubstituted or $C_1$–$C_4$alkyl-substituted $C_5$–$C_7$cycloalkyl; by unsubstituted or $C_1$–$C_4$alkyl-substituted phenyl; or by unsubstituted or $C_1$–$C_4$alkyl-substituted phenylene.

If $R_5$ and $R_6$, together with the linking carbon atoms, are unsubstituted $C_4$–$C_{11}$cycloalkenylene which is interrupted by oxygen, sulfur or

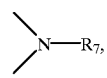

the ring of which is unsubstituted or substituted by $C_1$–$C_4$alkyl, by unsubstituted or $C_1$–$C_4$alkyl-substituted $C_5$–$C_{12}$cycloalkyl; by unsubstituted or $C_1$–$C_4$alkyl-substituted phenyl; or by unsubstituted or $C_1$–$C_4$alkyl-substituted phenylene, then this is typically

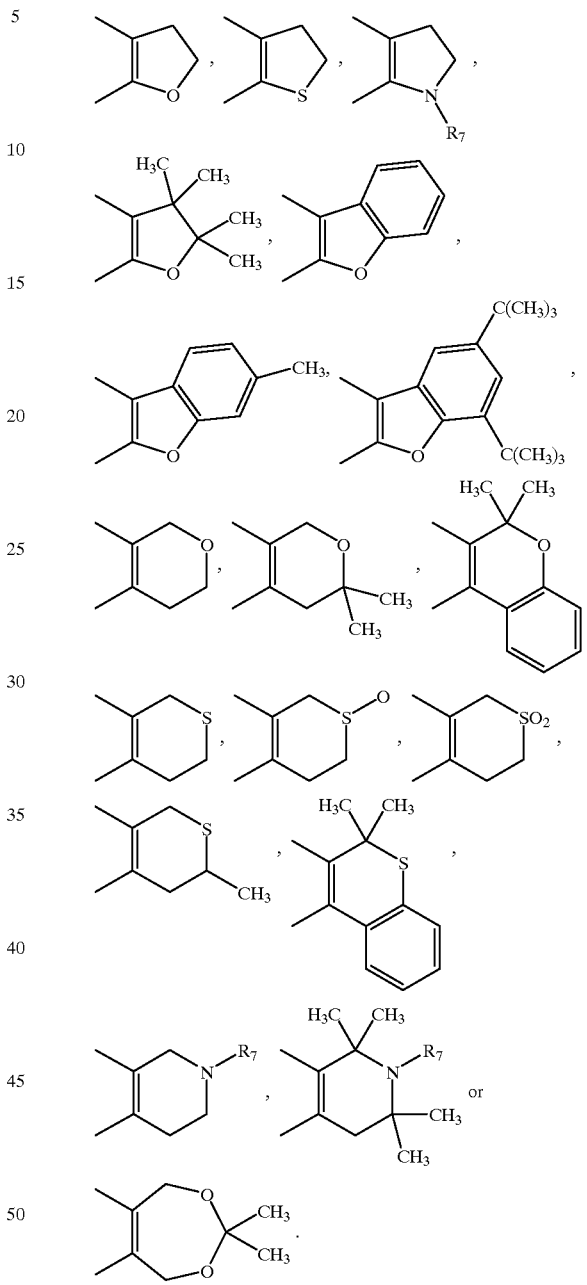

Together with the linking carbon atoms, $R_5$ and $R_6$ are preferably unsubstituted $C_4$–$C_8$cycloalkenylene which is interrupted by oxygen, sulfur or

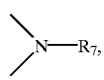

in particular $C_5$–$C_8$cycloalkenylene, e.g. $C_5$–$C_7$cycloalkenylene, the ring of which is unsubstituted or substituted by $C_1$–$C_4$alkyl, by unsubstituted or $C_1$–$C_4$alkyl-substituted cyclohexyl; by unsubstituted or $C_1$–$C_4$alkyl-substituted phenyl; or by unsubstituted or $C_1$–$C_4$alkyl-substituted phenylene.

Alkanoyl of up to 8 carbon atoms is a branched or unbranched radical, typically formyl, acetyl, propionyl, butanoyl, pentanoyl, hexanoyl, heptanoyl or octanoyl. It is preferred to use alkanoyl of 1 to 6, in particular of 1 to 4, e.g. of 1 to 3, carbon atoms. Acetyl is particularly preferred. $C_1$–$C_{12}$Alkyl-substituted benzoyl, which preferably carries 1 to 3, in particular 1 or 2, alkyl groups, is typically o-, m- or p-methylbenzoyl, 2,3-dimethylbenzoyl, 2,4-dimethylbenzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-tert-butylbenzoyl, 2-ethylbenzoyl, 2,4,6-trimethylbenzoyl, 2,6-dimethyl-4-tert-butylbenzoyl or 3,5-di-tert-butylbenzoyl. Preferred substituents are $C_1$–$C_8$alkyl, in particular $C_1$–$C_4$alkyl.

$C_5$–$C_{12}$Cycloalkenylene is an unsaturated hydrocarbon group containing a double bond and having two free valencies at the double bond and at least one ring unit, and is typically cyclopentenylene, cyclohexenylene, cycloheptenylene, cyclooctenylene, cyclononenylene, cyclodecenylene, cycloundecenylene or cyclododecenylene.

An unsubstituted or $C_1$–$C_4$alkyl-substituted $C_5$–$C_{12}$cycloalkylidene ring, which preferably carries 1 to 3, in particular 1 to 2, branched or unbranched alkyl groups, is typically cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. It is preferred to use an unsubstituted or $C_1$–$C_4$-alkyl-substituted $C_5$–$C_9$cycloalkylidene ring, in particular a $C_5$–$C_8$cycloalkylidene ring, e.g. a $C_5$–$C_7$cycloalkylidene ring. Cyclohexylidene and tert-butylcyclohexylidene are particularly preferred.

A mono-, di- or trivalent metal cation is preferably an alkali metal cation, an alkaline earth metal cation or an aluminium cation, typically $Na^+$, $K^+$, $Mg^{++}$, $Ca^{++}$ or $Al^{+++}$.

Preferred compounds are those of formula 1, wherein $R_2$ and $R_4$ are hydrogen.

Other preferred compounds are those of formula 1, wherein $R_5$ and $R_6$ are each independently of the other hydrogen, $C_1$–$C_4$alkyl or phenyl, or $R_5$ and $R_6$, together with the linking carbon atoms, are unsubstituted $C_5$–$C_7$cycloalkenylene or unsubstituted $C_5$–$C_6$cycloalkenylene which is interrupted by oxygen or sulfur, the rings of which are unsubstituted or substituted by $C_1$–$C_4$alkyl or phenyl.

Likewise preferred are the compounds of formula 1, wherein $R_1$, $R_2$, $R_3$ and $R_4$ are each independently of one another hydrogen, chloro, hydroxy, $C_1$–$C_{18}$alkyl; $C_2$–$C_{18}$alkyl which is interrupted by oxygen, sulfur or

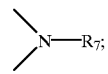

$C_2$–$C_{18}$alkenyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; unsubstituted or $C_1$–$C_4$alkyl-substituted $C_5$–$C_8$cycloalkenyl; $C_1$–$C_{18}$alkoxy, $C_2$–$C_{18}$alkenyloxy, $C_1$–$C_{18}$alkylthio, $C_1$–$C_4$alkylamino, di($C_1$–$C_4$alkyl)amino, $C_1$–$C_{18}$alkanoyloxy, $C_1$–$C_{18}$alkanoylamino, $C_3$–$C_{18}$alkenoyloxy; $C_3$–$C_{18}$alkanoyloxy which is interrupted by oxygen, sulfur or

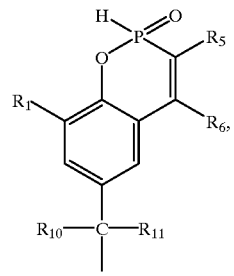

$C_5$–$C_9$cycloalkylcarbonyloxy, benzoyloxy or $C_1$–$C_4$alkyl-substituted benzoyloxy; or $R_1$ and $R_2$, or $R_2$ and $R_3$, or $R_3$ and $R_4$, together with the linking carbon atoms, form a benzene ring, $R_3$ additionally being —$(CH_2)_m$—$COR_8$ or —$(CH_2)_n OR_9$ or, if $R_2$ and $R_4$ are hydrogen, $R_3$ additionally being a radical of formula IIa

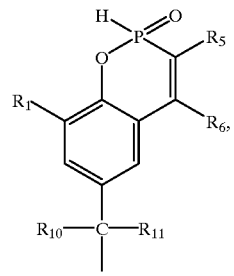

(IIa)

$R_5$ and $R_6$ are each independently of the other hydrogen, $C_1$–$C_{18}$alkyl; $C_2$–$C_{18}$alkyl which is interrupted by oxygen, sulfur or

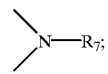

$C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl, or $R_5$ and $R_6$, together with the linking carbon atoms, are unsubstituted $C_5$–$C_9$cycloalkenylene or unsubstituted $C_4$–$C_8$cycloalkenylene which is interrupted by oxygen, sulfur or

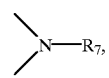

the rings of which are unsubstituted or substituted by $C_1$–$C_4$alkyl, by unsubstituted or $C_1$–$C_4$alkyl-substituted $C_5$–$C_8$cycloalkyl; by unsubstituted or $C_1$–$C_4$alkyl-substituted phenyl; or by phenylene, $R_7$ is hydrogen, $C_1$–$C_6$alkyl, $C_1$–$C_6$alkoxy, $C_1$–$C_6$alkanoyl or benzoyl, $R_8$ is hydroxy, $$\left[ -O^- \; \tfrac{1}{r} \; M^{r+} \right], C_1\text{-}C_{12}\text{alkoxy or } -N\!\!\begin{array}{c}R_{12}\\R_{13}\end{array},$$

$R_9$ is hydrogen, $C_1$–$C_8$alkanoyl or benzoyl, $R_{10}$ and $R_{11}$ are each independently of the other hydrogen, $CF_3$, $C_1$–$C_{10}$ alkyl, unsubstituted or $C_1$–$C_4$alkyl-substituted phenyl; or —$(CH_2)_s$—$COR_{14}$, or $R_{10}$ and $R_{11}$, together with the linking carbon atom, are a $C_5$–$C_9$cycloalkylidene ring which is unsubstituted or substituted by 1 to 3 $C_1$–$C_4$alkyl, $R_{12}$ and $R_{13}$ are each independently of the other hydrogen or $C_1$–$C_{12}$alkyl, $R_{14}$ is hydroxy, $C_1$–$C_{12}$alkoxy or

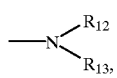

M is sodium, potassium, calcium or aluminium, m is 1 or 2, n is 2, 3, 4, 5 or 6, r is 1, 2 or 3, and s is 0 or 1.

Particularly preferred compounds are those of formula 1, wherein $R_1$, $R_2$, $R_3$ and $R_4$ are each independently of one another hydrogen, chloro, $C_1$–$C_{12}$alkyl, $C_2$–$C_{12}$alkyl which is interrupted by oxygen or sulfur; $C_2$–$C_{12}$alkenyl, $C_7$–$C_9$phenylalkyl, phenyl, $C_5$–$C_8$cycloalkyl, $C_5$–$C_8$cycloalkenyl, $C_1$–$C_{12}$alkoxy, $C_3$–$C_{12}$alkenyloxy, $C_1$–$C_{18}$alkylthio, $C_1$–$C_{12}$alkanoyloxy, $C_1$–$C_{12}$alkanoylamino, $C_3$–$C_{12}$alkenoyloxy; $C_3$–$C_{12}$alkanoyloxy which is interrupted by oxygen or sulfur; $C_5$–$C_8$cycloalkylcarbonyloxy or benzoyloxy;

$R_3$ additionally being a radical of formula IIa

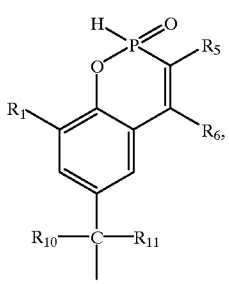

(IIa)

$R_5$ and $R_6$ are each independently of the other hydrogen, $C_1$–$C_{12}$alkyl; $C_2$–$C_{12}$alkyl which is interrupted by oxygen or sulfur; $C_7$–$C_9$phenylalkyl, phenyl or $C_5$–$C_8$cycloalkyl, or $R_5$ and $R_6$, together with the linking carbon atom, are unsubstituted $C_5$–$C_9$cycloalkenylene or $C_4$–$C_8$cycloalkenylene which is interrupted by oxygen or sulfur, the rings of which are unsubstituted or substituted by $C_1$–$C_4$alkyl, $C_5$–$C_8$cycloalkyl or phenyl, $R_{10}$ and $R_{11}$ are each independently of the other hydrogen, $CF_3$, $C_1$–$C_8$alkyl, phenyl or —$(CH_2)_s$—$COR_{14}$, or $R_{10}$ and $R_{11}$, together with the linking carbon atom, are a $C_5$–$C_9$cycloalkylidene ring, $R_{14}$ is hydroxy or $C_1$–$C_{12}$alkoxy, and s is 0 or 1.

Particularly interesting compounds of formula I are those, wherein $R_1$ is hydrogen, $C_1$–$C_4$alkyl, cyclohexyl, 1-cyclohexenyl or $C_7$–$C_9$phenylalkyl, $R_2$ is hydrogen, $R_3$ is hydrogen, $C_1$–$C_4$alkyl, cyclohexyl, 2-cyclohexenyl, $C_7$–$C_9$phenylalkyl or $C_1$–$C_4$alkoxy, $R_4$ is hydrogen, and $R_5$ and $R_6$ are each independently of the other hydrogen, $C_1$–$C_4$alkyl or phenyl, or $R_5$ and $R_6$, together with the linking carbon atoms, are unsubstituted $C_5$–$C_7$cycloalkenylene or unsubstituted $C_5$–$C_6$cycloalkenylene which is interrupted by oxygen or sulfur, the rings of which are unsubstituted or substituted by $C_1$–$C_4$alkyl or phenyl.

Very particularly interesting compounds of formula I are those, wherein $R_1$ is hydrogen, $C_1$–$C_4$alkyl or $C_7$–$C_9$phenylalkyl, $R_2$ is hydrogen, $R_3$ is $C_1$–$C_4$alkyl, $C_7$–$C_9$phenylalkyl or $C_1$–$C_4$alkoxy, $R_4$ is hydrogen, and $R_5$ and $R_6$ are each independently of the other hydrogen or phenyl, or $R_6$ and $R_6$, together with the linking carbon atoms, are unsubstituted $C_5$–$C_7$cycloalkenylene or unsubstituted $C_5$-cycloalkenylene which is interrupted by oxygen or sulfur, the rings of which are unsubstituted or substituted by $C_1$–$C_4$alkyl.

There is no process disclosed in the literature for the preparation of the novel compounds of formula I.

Accordingly, this invention also relates to a process for the preparation of compounds of formula I

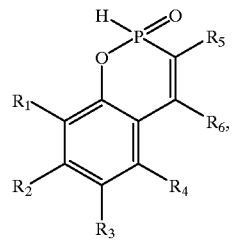

(I)

wherein the general symbols have the cited meanings, which process comprises reacting a compound of formula III

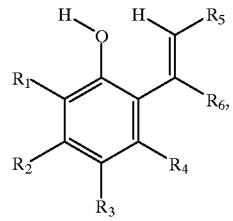

(III)

wherein the general symbols have the cited meanings, with phosphorus trichloride to a compound of formula IV

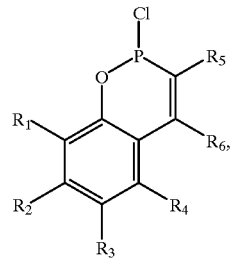

(IV)

wherein the general symbols have the cited meanings, and subsequently hydrolysing this compound with water without isolation.

The compounds of formula IV can be isolated and characterised.

The compound of formula III is reacted with phosphorus trichloride in the melt or in the presence of a suitable organic, polar or apolar, aprotic solvent. This reaction is preferably carried out in the temperature range from -20° C. and the boiling point of the solvent or of phosphorus trichloride, in particular in the range from 20 and 200° C., e.g. from 20 and 150° C. This reaction is particularly preferably carried out without solvent. The phosphorus trichloride is in this case solvent as well as reaction partner. The phosphorus trichloride is preferably used at a molar excess relative to the compound of formula II. A particularly interesting molar ratio of the compound of formula III to phosphorus trichloride is that from 1:20 to 1:1, in particular from 1:10 to 1:1, e.g. from 1:5 to 1:1.

Suitable solvents for carrying out the reaction are, inter alia, hydrocarbons (for example mesitylene, toluene, hexane, pentane or other petroleum ether fractions), halogenated hydrocarbons (for example di- or trichloromethane, 1,2-dichloroethane, 1,1,1-trichloroethane or chlorobenzene), ethers (e.g. diethyl ether, dibutyl ether, dioxane or tetrahydrofuran), ketones (e.g. acetone, ethyl methyl ketone, diethyl ketone, methyl propyl ketone or cyclohexanone), and also acetonitrile or butylacetate. A particularly preferred solvent is toluene.

It is remarkable that the compounds of formula III are reacted with phosphorus trichloride to the compounds of formula IV without any catalysts, such as Friedel-Crafts catalysts, in particular aluminium chloride, already within relatively short reaction times.

The reaction of the compounds of formula III with phosphorus trichloride to the compounds of formula IV can also be carried out in the presence of a base.

The base can be used in different amounts, in the range from catalytic to stoichiometric amounts up to a multiple molar excess relative to the compounds of formula III used. The hydrogen halide formed during the reaction is, where appropriate, converted by the base into a halide which can be removed by filtration and/or washing with a suitable aqueous or solid phase; in this case a second, water-immiscible solvent may also be used. The products are conveniently isolated by concentrating the organic phase by evaporation and then drying the residue.

Suitable bases are, inter alia, primary, secondary or, especially, tertiary, amines (e.g. trimethylamine, triethylamine, tributylamine, N,N-dimethylaniline, N,N-diethylaniline or pyridine), alcoholates (e.g. sodium methanolate) or alkali carbonates (e.g. sodium carbonate or potassium carbonate). Tertiary amines are particularly preferred, in particular triethylamine.

Hydrolysing the compounds of formula IV with water to the compounds of formula I is preferably carried out in the temperature range from -20 to 150° C., in particular from -10 to 120° C., e.g. from 0 to 1 10° C. In this case the water can be used in high molar excess relative to the compound of formula IV. In a particularly preferred embodiment of this invention, the hot crude reaction mixture, which comprises the compounds of formula IV, is poured without processing into a high excess of water. The compounds of formula I then crystallise out or can be extracted with a suitable solvent, such as ethyl acetate, diethyl ether or dichloromethane.

The compounds of formula IV are not known in the literature.

Accordingly, this invention also relates to novel compounds of formula IV

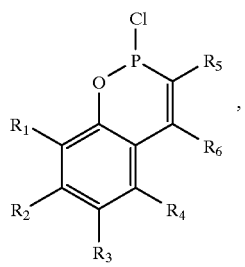

(IV)

wherein $R_1$, $R_2$, $R_3$ and $R_4$ are each independently of one another hydrogen, halogen, hydroxy, $C_1$–$C_{25}$alkyl; $C_2$–$C_{25}$alkyl which is interrupted by oxygen, sulfur or

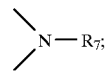

$C_2$–$C_{24}$alkenyl, $C_7$–$C_9$phenylalkyl, unsubstituted or $C_1$–$C_4$alkyl-substituted phenyl; unsubstituted or $C_1$–$C_4$alkyl-substituted $C_5$–$C_{12}$cycloalkyl; unsubstituted or $C_1$–$C_4$alkyl-substituted $C_5$–$C_{12}$cycloalkenyl; $C_1$–$C_{18}$alkoxy, $C_2$–$C_{24}$alkenyloxy, $C_1$–$C_{18}$alkylthio, $C_1$–$C_4$alkylamino, di($C_1$–$C_4$alkyl)amino, $C_1$–$C_{25}$alkanoyloxy, $C_1$–$C_{25}$alkanoylamino, $C_3$–$C_{25}$alkenoyloxy; $C_3$–$C_{25}$alkanoyloxy which is interrupted by oxygen, sulfur or

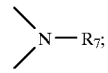

$C_5$–$C_9$cycloalkylcarbonyloxy, benzoyloxy or $C_1$–$C_{12}$alkyl-substituted benzoyloxy; or $R_1$ and $R_2$, or $R_2$ and $R_3$, or $R_3$ and $R_4$, together with the linking carbon atoms, are a benzene ring, $R_3$ additionally being —(CH$_2$)$_m$—COR$_8$ or —(CH$_2$)$_s$OR$_9$ or, if $R_2$ and $R_4$ are hydrogen, $R_3$ additionally being a radical of formula IIa, IIb or IIc

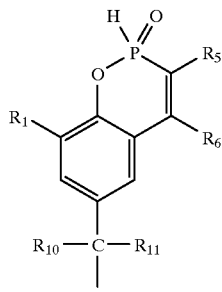

(IIa)

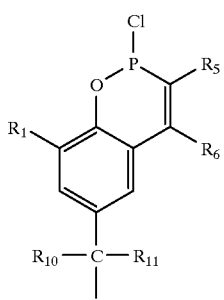

(IIb)

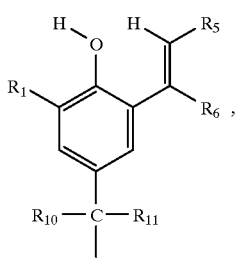

(IIc)

$R_5$ and $R_6$ are each independently of the other hydrogen, $C_1$–$C_{25}$alkyl; $C_2$–$C_{25}$alkyl which is interrupted by oxygen, sulfur or

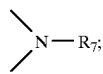

$C_7$–$C_9$phenylalkyl, unsubstituted or $C_1$–$C_4$alkyl-substituted phenyl; unsubstituted or $C_1$–$C_4$alkyl-substituted $C_5$–$C_{12}$cycloalkyl, or $R_5$ and $R_6$, together with the linking carbon atoms, are unsubstituted $C_5$–$C_{12}$cycloalkenylene or unsubstituted $C_4$–$C_{11}$cycloalkenylene which is interrupted by oxygen, sulfur or

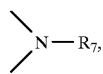

the rings of which are unsubstituted or substituted by $C_1$–$C_4$alkyl, by unsubstituted or $C_1$–$C_4$alkyl-substituted $C_5$–$C_{12}$cycloalkyl; by unsubstituted or $C_1$–$C_4$alkyl-substituted phenyl; or by unsubstituted or $C_1$–$C_4$alkyl-substituted phenylene, $R_7$ is hydrogen, $C_1$–$C_8$alkyl, $C_1$–$C_8$alkoxy, $C_1$–$C_8$alkanoyl or unsubstituted or $C_1$–$C_4$alkyl-substituted benzoyl, $R_8$ is hydroxy,

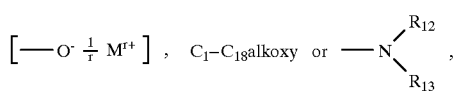

$R_9$ is hydrogen, $C_1$–$C_8$alkanoyl or unsubstituted or $C_1$–$C_4$alkyl-substituted benzoyl, $R_{10}$ and $R_{11}$ are each independently of the other hydrogen, $CF_3$, $C_1$–$C_{12}$alkyl, unsubstituted or $C_1$–$C_4$alkyl-substituted phenyl; or —$(CH_2)_s$—$COR_{14}$, or $R_{10}$ and $R_{11}$, together with the linking carbon atom, are a $C_5$–$C_{12}$cycloalkylidene ring which is unsubstituted or substituted by 1 to 3 $C_1$–$C_4$alkyl, $R_{12}$ and $R_{13}$ are each independently of the other hydrogen or $C_1$–$C_{18}$alkyl, $R_{14}$ is hydroxy, $C_1$–$C_{18}$alkoxy

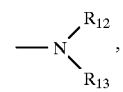

M is an r-valent metal cation, m is 0, 1 or 2, n is 1, 2, 3, 4, 5 or 6, r is 1, 2 or 3, and s is 0 or 1.

Preferred groups of novel compounds of formula IV correspond to the preferences stated above for the compounds of formula I.

Some of the compounds of formula III are known from the literature and can be prepared in general analogy to U.S. Pat. No. 5,414,033, Example 1; or EP-A-0 705 870.

In another of its aspects, this invention therefore also relates to novel compounds of formula III

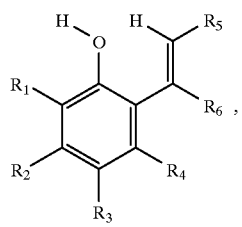

(III)

wherein $R_1$, $R_2$, $R_3$ and $R_4$ are each independently of one another hydrogen, halogen, hydroxy, $C_1$–$C_{25}$alkyl; $C_2$–$C_{25}$alkyl which is interrupted by oxygen, sulfur or

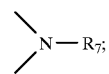

$C_2$–$C_{24}$alkenyl, $C_7$–$C_9$phenylalkyl, unsubstituted or $C_1$–$C_4$alkyl-substituted phenyl; unsubstituted or $C_1$–$C_4$alkyl-substituted $C_5$–$C_{12}$cycloalkyl; unsubstituted or $C_1$–$C_4$alkyl-substituted $C_5$–$C_{12}$cycloalkenyl; $C_1$–$C_{18}$alkoxy, $C_2$–$C_{24}$alkenyloxy, $C_1$–$C_{18}$alkylthio, $C_1$–$C_4$alkylamino, di($C_1$–$C_4$alkyl)amino, $C_1$–$C_{25}$alkanoyloxy, $C_1$–$C_{25}$alkanoylamino, $C_3$–$C_{25}$alkenoyloxy; $C_3$–$C_{25}$alkanoyloxy which is interrupted by oxygen, sulfur or

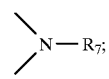

$C_5$–$C_9$cycloalkylcarbonyloxy, benzoyloxy or $C_1$–$C_{12}$alkyl-substituted benzoyloxy; or $R_1$ and $R_2$, or $R_2$ and $R_3$, or $R_3$ and $R_4$, together with the linking carbon atoms, are a benzene ring, $R_3$ additionally being —$(CH_2)_m$—$COR_8$ or —$(CH_2)_nOR_9$ or, if $R_2$ and $R_4$ are hydrogen, $R_3$ additionally being a radical of formula IIa, IIb or IIc

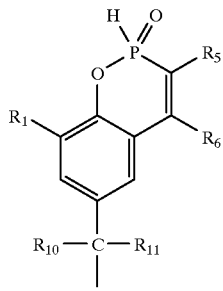
(IIa)

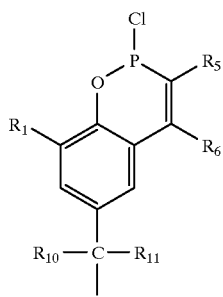
(IIb)

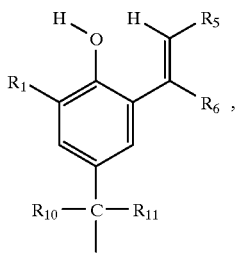
(IIc)

$R_5$ and $R_6$, together with the linking carbon atoms, are unsubstituted cyclopentenylene or $C_7$–$C_{12}$cycloalkenylene or unsubstituted $C_4$–$C_{11}$cycloalkenylene which is interrupted by oxygen, sulfur or

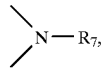

the rings of which are unsubstituted or substituted by $C_1$–$C_4$alkyl, by unsubstituted or $C_1$–$C_4$alkyl-substituted $C_5$–$C_{12}$cycloalkyl; by unsubstituted or $C_1$–$C_4$alkyl-substituted phenyl; or by unsubstituted or $C_1$–$C_4$alkyl-substituted phenylene, $R_7$ is hydrogen, $C_1$–$C_8$alkyl, $C_1$–$C_8$alkoxy, $C_1$–$C_8$alkanoyl or unsubstituted or $C_1$–$C_4$alkyl-substituted benzoyl, $R_8$ is hydroxy,

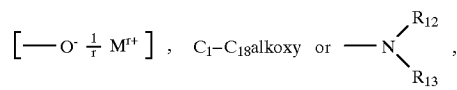

$R_9$ is hydrogen, $C_1$–$C_8$alkanoyl or unsubstituted or $C_1$–$C_4$alkyl-substituted benzoyl, $R_{10}$ and $R_{11}$ are each independently of the other hydrogen, $CF_3$, $C_1$–$C_{12}$alkyl, unsubstituted or $C_1$–$C_4$alkyl-substituted phenyl; or —$(CH_2)_s$—$COR_{14}$, or $R_{10}$ and $R_{11}$, together with the linking carbon atom, are a $C_5$–$C_{12}$cycloalkylidene ring which is unsubstituted or substituted by 1 to 3 $C_1$–$C_4$alkyl, $R_{12}$ and $R_{13}$ are each independently of the other hydrogen or $C_1$–$C_{18}$alkyl, $R_{14}$ is hydroxy, $C_1$–$C_{18}$alkoxy or

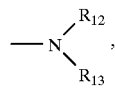

M is an r-valent metal cation, m is 0, 1 or 2, n is 1, 2, 3, 4, 5 or 6, r is 1, 2 or 3, and s is 0 or 1.

Preferred groups of novel compounds of formula III correspond to the preferences stated above for the compounds of formula I.

Particularly preferred compounds of formula III are those, wherein $R_1$ is hydrogen, $C_1$–$C_4$alkyl or $C_7$–$C_9$phenylalkyl, $R_2$ is hydrogen, $R_3$ is $C_1$–$C_4$alkyl, $C_7$–$C_9$phenylalkyl or $C_1$–$C_4$alkoxy, $R_4$ is hydrogen, and $R_5$ and $R_6$, together with the linking carbon atoms, are unsubstituted cyclopentenylene or cycloheptenylene or unsubstituted $C_5$-cycloalkenylene which is interrupted by oxygen or sulfur, the rings of which are unsubstituted or substituted by $C_1$–$C_4$alkyl.

The preparation of the novel compounds of formula III is preferably carried out, for example, by condensing the phenols of formula V

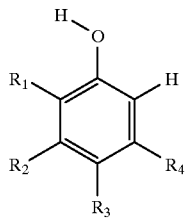
(V)

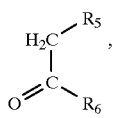

(VI)

which are unsubstituted in at least one ortho-position, with a ketone of formula VI, wherein the general symbols have the cited meanings. The reaction is carried out at elevated temperature, in particular in the range from 20 to 100° C., in the melt or in a solvent, if required under slight pressure. The reaction is preferably carried out in the melt in the temperature range from 20 to 80° C., in particular from 30 to 60° C. It is possible to catalyse the reaction by adding an acid, such as hydrochloric acid, sulfuric acid or methanesulfonic acid. It is preferred to use hydrochloric acid gas.

The novel compounds of formula I are suitable for stabilising organic materials against oxidative, thermal or light-induced degradation.

Illustrative examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EM), LLDPE/EVA, LLDPE/EM and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrenelethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

In another of its aspects, this invention therefore also relates to compositions comprising (a) an organic material which is subject to oxidative, thermal or light-induced degradation, and (b) at least one compound of formula I.

The organic materials to be protected are preferably natural, semi-synthetic or, preferably, synthetic polymers. Thermoplastic polymers are particularly preferred, especially PVC or polyolefins, most preferably polyethylene and polypropylene. Of particular interest is also a copolymer or graft copolymer of styrene or a-methylstyrene with dienes, polybutadiene or acrylic derivatives. An ABS injection moulding composition is very particularly preferred.

To be highlighted in particular is the action of the novel compounds against thermal and oxidative degradation, in particular under thermal stress, as is the case when processing thermoplastic materials. The novel compounds can therefore be excellently used as processing stabilisers.

The compounds of formula I are preferably added to the material to be stabilised in amounts of 0.01 to 10%, typically of 0.01 to 5%, preferably of 0.025 to 3%, in particular of 0.025 to 1%, based on the weight of the organic material to be stabilised.

In addition to the compounds of formula 1, the novel compositions can comprise additional costabilisers (additives), for example the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6- dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris (3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4 -hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis( 1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialkylated nonyidiphenylamines, a mixture of mono- and dialkylated dodecyldiphenylamines, a mixture of mono- and dialkylated isopropyllisohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-( 1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$]$_2$— where R=3'-tert-butyl-4'-hydroxy-5'-2H-benzotriazol-2-ylphenyl, 2-[2'-hydroxy-3'-(α,α-dimethylbenzyl)-5'-( 1,1,3,3-tetramethylbutyl)-phenyl]benzotriazole; 2-[2'-hydroxy-3'-( 1,1,3,3-tetramethylbutyl)-5'-(α,α-dimethylbenzyl)-phenyl] benzotriazole. 2.2.2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyidithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis( 1,2,2,6,6-pentamethyl-4-piperidyl) sebacate, bis( 1-octyloxy-2,2,6,6-tetramethyl-4-piperidyl) sebacate, bis(1,2,2,6,6-pentamethyl-4-piperidyl) n-butyl-3, 5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1, 2,3,4-butane-tetracarboxylate, 1,1'-(1,2-ethanediyl)-bis(3,3, 5,5-tetramethylpiperazinone), 4-benzoyl-2,2,6,6-tetramethylpiperidine, 4-stearyloxy-2,2,6,6-tetramethylpiperidine, bis( 1,2,2,6,6-pentamethylpiperidyl)-

2-n-butyl-2-(2-hydroxy-3,5-di-tert-butylbenzyl)malonate, 3-n-octyl-7,7,9,9-tetramethyl-1,3,8-triazaspiro[4,5]decan-2,4-dione, bis( 1-octyloxy-2,2,6,6-tetramethylpiperidyl) sebacate, bis( 1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl )-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-l-(2,2,6,6-tetramethyl-4 -piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl4-piperidyl)-n-dodecylsuccinimid, 2-undecyl-7,7,9,9-tetramethyl-1-oxa-3,8-diaza-4-oxo-spiro[4,5ldecane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxymethylenemalonic acid with 1,2,2,6,6-pentamethyl-4-hydroxypiperidine, polylmethylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxvphenvl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis-(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3 -butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide. 4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, tristearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol di-phosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-di-benz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-di-yl)phosphite.

Especially preferred are the following phosphites:

Tris(2,4-di-tert-butylphenyl) phosphite (Irgafos®168, Ciba-Geigy), tris(nonylphenyl) phosphite,

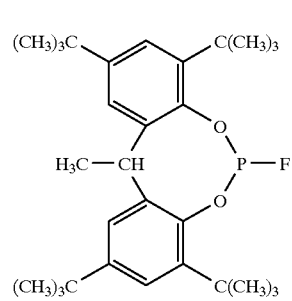

(A)

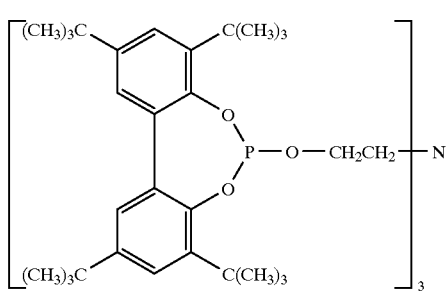
(B)

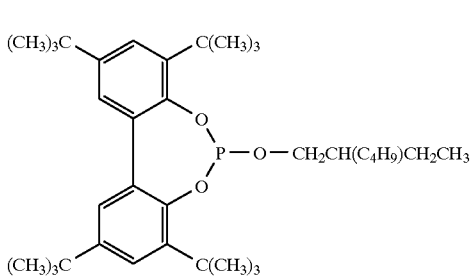
(C)

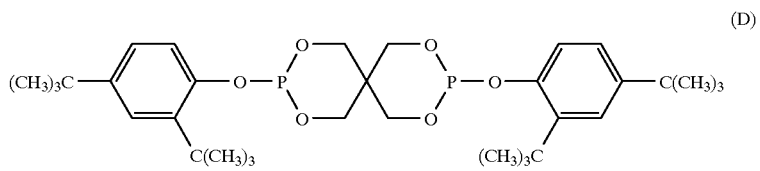
(D)

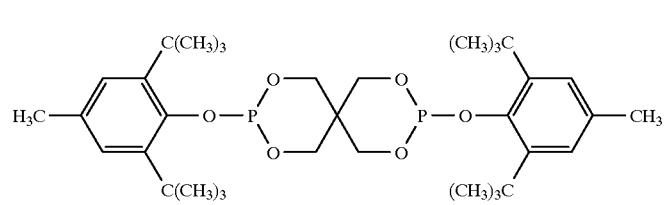
(E)

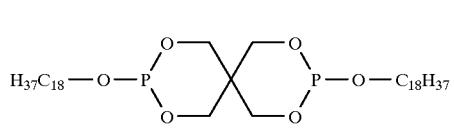
(F)

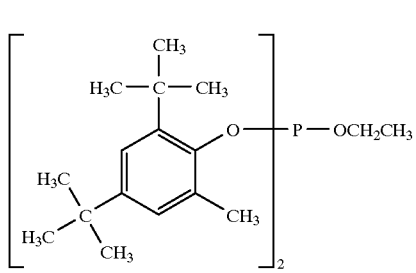
(G)

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-oc-tyl-alpha-heptyl-nitrone, N-lauryl-alpha-undecyl-nitrone, N-tetradecyl-alpha-tridcyl-nitrone, N-hexadecyl-alpha-pentadecylnitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyidithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-di-methylphenyl)-5,7-di-tert-butyl-benzofuran-2-one.

The costabilisers, with the exception of the benzofuranones listed under item 14, are typically added in concentrations of 0.01 to 10%, based on the total weight of the organic materials to be stabilised.

Other preferred compositions comprise, besides component (a) and the compounds of formula 1, additional additives, in particular phenolic antioxidants, light stabilisers or/and processing stabilisers.

Particularly preferred additives are phenolic antioxidants (item 1 of the list), sterically hindered amines (item 2.6 of the list), phosphites and phosphonites (item 4 of the list) and peroxide scavengers (item 8 of the list).

Other particularly preferred additional additives (stabilisers) are benzofuran-2-ones, such as those disclosed e.g. in U.S. Pat. Nos. 4,325,863, 4,338,244, 5,175,312, 5,216,052, 5,252,643, DE-A-4 316 611, DE-A-4 316 622, DE-A-4 316 876, EP-A-0 589 839 and EP-A-0591 102.

Typical examples of such benzofuran-2-ones are compounds of formula

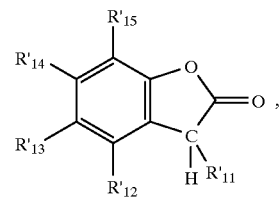

wherein $R'_{11}$ is an unsubstituted or substituted carbocyclic or heterocyclic aromatic ring system;

$R'_{12}$ is hydrogen;

$R'_{14}$ is hydrogen, alkyl of 1 to 12 carbon atoms, cyclopentyl, cyclohexyl or chloro;

$R'_{13}$ has the meaning of $R'_{12}$ or $R'_{14}$ or is a radical of formula

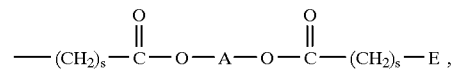

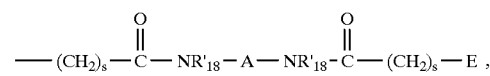

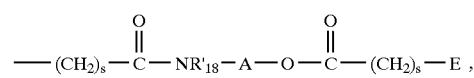

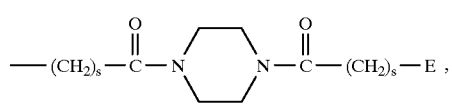

wherein $R'_{16}$ is hydrogen, alkyl of 1 to 18 carbon atoms; alkyl of 2 to 18 carbon atoms which is interrupted by oxygen or sulfur, dialkylaminoalkyl containing a total of 3 to 16 carbon atoms, cyclopentyl, cyclohexyl, phenyl, or phenyl which is substituted by 1 to 3 alkyl radicals containing together no more than 18 carbon atoms;

s is 0, 1 or 2;

the substituents $R'_{17}$ are each independently of one another hydrogen, alkyl of 1 to 18 carbon atoms, cyclopentyl, cyclohexyl, phenyl, phenyl which is substituted by I or 2 alkyl radicals containing together no more than 16 carbon atoms, a radical of formula —C₂H₄OH, —C₂H₄—O—C$_t$H$_{2t+1}$ or

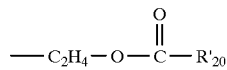

or, together with the linking nitrogen atom, form a piperidine radical or morpholine radical;

t is 1 to 18;

R'$_{20}$ is hydrogen, alkyl of 1 to 22 carbon atoms or cycloalkyl of 5 to 12 carbon atoms;

A is alkylene of 2 to 22 carbon atoms which may be interrupted by nitrogen, oxygen or sulfur;

R'$_{18}$ is hydrogen, alkyl of 1 to 18 carbon atoms, cyclopentyl, cyclohexyl, phenyl; phenyl or benzyl which is substituted by 1 or 2 alkyl radical containing together no more than 16 carbon atoms;

R'$_{19}$ is alkyl of 1 to 18 carbon atoms;

D is —O—, —S—, —SO—, —SO₂— or —C(R'$_{21}$)₂—;

the substituents R'$_{21}$ are each independently of the other hydrogen, C₁–C₁₆alkyl, the two R'$_{21}$ containing together 1 to 16 carbon atoms, R'$_{21}$ also being phenyl or a radical of formula

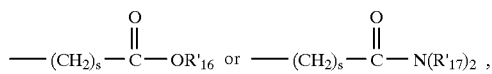

wherein s, R'$_{16}$ and R'$_{17}$ have the meanings cited above;

E is a radical of formula

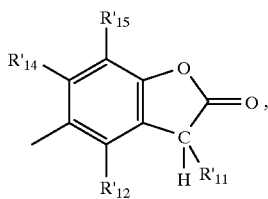

wherein R'$_{11}$, R'$_{12}$ and R'$_{14}$ have the meanings cited above; and

R'$_{15}$ is hydrogen, alkyl of 1 to 20 carbon atoms, cyclopentyl, cyclohexyl, chloro or a radical of formula

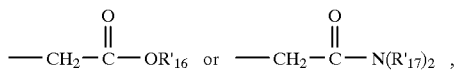

wherein R'$_{16}$ and R'$_{17}$ have the meanings cited above, or R'$_{15}$, together with R'$_{14}$, is a tetramethylene radical.

Those benzofuran-2-ones are preferred, wherein R'$_{13}$ is hydrogen, alkyl of 1 to 12 carbon atoms, cyclopentyl, cyclohexyl, chloro or a radical of formula

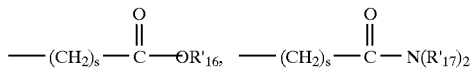

or —D—E, wherein s, R'$_{16}$, R'$_{17}$, D and E have the meanings given above, R'$_{16}$ preferably being hydrogen, alkyl of 1 to 18 carbon atoms, cyclopentyl or cyclohexyl.

Other preferred benzofuran-2-ones are those, wherein R'$_{11}$ is phenyl, or phenyl which is substituted by 1 or 2 alkyl radicals containing together no more than 12 carbon atoms; R'$_{12}$ is hydrogen; R'$_{14}$ is hydrogen or alkyl of 1 to 12 carbon atoms;

R'$_{13}$ is hydrogen, alkyl of 1 to 12 carbon atoms,

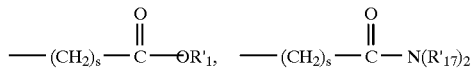

or —D—E; R'$_{15}$ is hydrogen, alkyl of 1 to 20 carbon atoms,

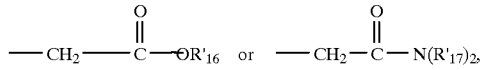

or R'$_{15}$, together with R'$_{14}$, is a tetramethylene radical, s, R'$_{16}$, R'$_{17}$, D and E having the meanings stated at the outset.

Particularly interesting benzofuran-2-ones are also those, wherein R'$_{13}$ is hydrogen, alkyl of 1 to 12 carbon atoms or —D—E; R'$_{12}$ and R'$_{14}$ are each independently of the other hydrogen or alkyl of 1 to 4 carbon atoms; and R'$_{15}$ is alkyl of 1 to 20 carbon atoms, D and E having the meanings stated at the outset.

Of special interest are, finally, also those benzofuran-2-ones, wherein R'$_{13}$ is alkyl of 1 to 4 carbon atoms or —D—E; R'$_{12}$ and R'$_{14}$ are hydrogen; and R'$_{15}$ is alkyl of 1 to 4 carbon atoms, cyclopentyl or cyclohexyl, D being a group —C(R'$_{21}$)₂— and E a radical of formula

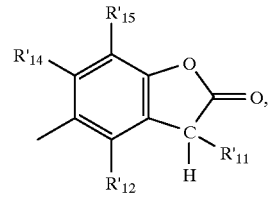

the substituents R'$_{21}$ are identical or different and are each alkyl of 1 to 4 carbon atoms, and R'$_{11}$, R'$_{12}$, R'$_{14}$ and R'$_{15}$ have the given meanings.

The amount of additionally added benzofuran-2-ones can vary within wide limits and they may be present in the compositions of this invention in amounts of, for example, 0.0001 to 5% by weight, preferably of 0.001 to 2% by weight, more preferably of 0.01 to 2% by weight.

The incorporation of the compounds of formula I and optional further additives into the polymeric organic material is carried out by known methods, for example before or after moulding or also by applying the dissolved or dispersed stabiliser mixture to the polymeric organic material, with or without subsequent evaporation of the solvent. The compounds of formula I can also be added to the materials to be stabilised in the form of a masterbatch which contains these components in a concentration of, for example, 2.5 to 25% by weight.

The compounds of formula I can also be added before or during polymerisation or before crosslinking.

The compounds of formula I can be incorporated into the material to be stabilised in pure form or encapsulated in waxes, oils or polymers.

The compounds of formula I can also be sprayed onto the polymer to be stabilised. They are able to dilute other additives (e.g. the conventional additives indicated above) or their melts so that they can be sprayed also together with these additives onto the polymer to be stabilised. Addition by spraying during the deactivation of the polymerisation catalysts is particularly advantageous, it being possible to carry out spraying using, for example, the steam used for deactivation.

In the case of spherically polymerised polyolefins it may, for example, be advantageous to apply the compounds of formula 1, optionally together with other additives, by spraying.

The materials thus stabilised can be used in a very wide range of forms, typically including films, fibres, filaments, moulded articles, profiles or as binders for paint systems, in particular powder coating compositions, adhesives or putties.

As already mentioned, the organic materials to be protected are preferably organic, more preferably synthetic, polymers. Thermoplastic materials are particularly advantageously protected. To be highlighted in this connection is in particular the excellent action of the novel compounds of formula I as processing stabilisers (heat stabilisers). For this purpose, they are usefully added to the polymer before or during processing. However, other polymers (e.g. elastomers) or lubricants or hydraulic fluids can also be stabilised against degradation, such as light-induced or thermo-oxidative degradation. Examples of elastomers will be found in the above list of possible organic materials.

Suitable lubricants and hydraulic fluids may be based on mineral or synthetic oils, or mixtures thereof. The lubricants are known to the person skilled in the art and are described in the relevant technical literature, for example in Dieter Klamann, "Schmierstoffe und verwandte Produkte" (Verlag Chemie, Weinheim, 1982), in Schewe-Kobek, "Das Schmiermittel-Taschenbuch" (Dr. Alfred Hüthig-Verlag, Heidelberg, 1974) and in "Ullmanns Enzyklopädie der technischen Chemie", Vol. 13, pages 85–94 (Verlag Chemie, Weinheim, 1977).

Accordingly, a preferred embodiment of this invention is the use of compounds of formula I as stabilisers, in particular as processing stabilisers (heat stabilisers), for stabilising organic materials, in particular thermoplastic polymers, against oxidative, thermal or light-induced degradation.

The novel compounds of formula I are distinguished by their markedly good stability to hydrolysis and their advantageous colour behaviour, i.e. minor discolouration of the organic materials during processing.

Organic materials stabilised with the novel compounds are particularly well protected against light-induced degradation.

Accordingly, this invention also relates to a process for stabilising an organic material against oxidative, thermal or light-induced degradation, which process comprises incorporating in, or applying to, said material at least one compound of formula 1.

The following Examples illustrate the invention in greater detail. Parts and percentages are by weight.

EXAMPLE 1

Preparation of the Compounds of Formula III
(Table 1)

a) Preparation of compound (101) (Table 1).

A mixture consisting of 82.5 g (0.40 mol) of 2,4-di-tert-butylphenol and 16.8 g (0.20 mol) of cyclopentanone is melted together and is then saturated, with stirring, with hydrochloric acid gas at 40–45° C. After 22 hours, the dark brown reaction mixture is diluted with hexane and washed with water and sodium chloride solution. The organic phase is dried over magnesium sulfate and is concentrated on a vacuum rotary evaporator. The residue is distilled under vacuum, giving 11.5 g (21%) of 2,4-di-tert-butyl-6-cyclopenten-lyl-phenol, m.p. 98–112° C./0.08 mbar, a yellowish oil (compound (101), Table 1).

b) Preparation of compound (102) (Table 1).

24.75 g (120 mmol) of 2,4-di-tert-butylphenol and 2.95 g (30.0 mmol) of cyclohexanone are melted together at 60° C. The melt is then cooled to 45° C., saturated with hydrochloric acid gas and stirred for 24 hours at 45° C. The reaction mixture is charged with 50 ml of methanol and is then cooled with ice/water. The precipitated product is filtered and washed with a small amount of cold methanol, affording 4.55 g of the product. The filtrate is concentrated on a vacuum rotary evaporator, and excess 2,4-di-tert-butylphenol is removed by distillation under high vacuum. The residue is crystallised from 10 ml methanol, affording another 1.75 g of the product. A total of 6.3 g (73%) of 2,4-di-tert-butyl-6-cyclohexen-1-yl-phenol, m.p. 102–104° C. (compound (101), Table 1), are thus obtained.

c) Preparation of compound (103) (Table 1).

A mixture consisting of 21.9 g (0.106 mol) of 2,4-di-tert-butylphenol, 5.3 g (0.053 mol) of tetrahydro-4H-pyran-4-one and 5 ml of acetic acid is melted melted together and is then saturated, with stirring, with hydrochloric acid gas at 40–45° C. After standing for 60 hours at room temperature, the reaction mixture is diluted with toluene and washed with water, sodium chloride solution and sodium hydrogencarbonate solution. The organic phase is dried over magnesium sulfate and concentrated on a rotary evaporator. The residue is crystallised from methanol, giving 7.2 g (47%) of 2,4-di-tert-butyl-6-(3,6-dihydro-2H-pyran-4-yl)phenol, m.p. 135–139° C. (compound (103), Table 1).

d) Preparation of compound (104) (Table 1).

A mixture consisting of 17 g (0.082 mol) of 2,4-di-tert-butylphenol, 4.8 g (0.041 mol) of tetrahydrothiopyran-4-one and 5 ml of acetic acid is melted together and is then saturated, with stirring, with hydrochloric acid gas at 40–45° C. After stirring for 12 hours at room temperature, the reaction mixture is diluted with toluene and washed with water, sodium chloride solution and sodium hydrogencarbonate solution. The organic phase is dried over magnesium sulfate and concentrated on a rotary-evaporator. The residue is crystallised from methanol, affording 9.2 g (74%) of 2,4-di-tert-butyl-6-(3,6-dihydro-2H-thiopyran-4-yl)phenol, m.p. 115–119° C. (compound (104), Table 1).

e) Preparation of compound (105) (Table 1).

A mixture consisting of 82.5 g (0.40 mol) of 2,4-di-tert-butylphenol and 22.5 g (0.20 mol) of cycloheptanone is melted together and is then saturated, with stirring, with hydrochloric acid gas at 35–40° C. After 22 hours, the reaction mixture is again saturated with hydrochloric acid gas and then stirred for 17 hours. Subsequently, the reaction mixture is diluted with hexane and washed with water and sodium chloride solution. The organic phase is dried over magnesium sulfate and concentrated on a rotary evaporator. The residue is chromatographed over silica gel using the solvent system hexane/ethyl acetate=99:1 and the pure fractions are crystallised from ethanol, giving 5.4 g (9%) of 2,4-di-tert-butyl-6-cyclohepten-1-yl-phenol, m.p. 78–80° C. (compound (105), Table 1).

f) Preparation of compound (106) (Table 1).

A mixture consisting of 30.9 g (0.15 mol) of 2,4-di-tert-butylphenol and 10.5 g (0.075 mol) of 3,3,5-trimethylcyclohexanone is melted together and is then saturated, with stirring, with hydrochloric acid gas at 35° C. After 24 hours, the reaction mixture is again saturated with hydrochloric acid gas and is then stirred for 20 hours.

Subsequently, the green reaction mixture is diluted with hexane and washed with water and sodium chloride solution. The organic phase is dried over magnesium sulfate and concentrated on a rotary evaporator. The residue is chromatographed over silica gel using the solvent system hexane/ethyl acetate=49:1, giving 10.6 g (43%) of 2,4-di-tert-butyl-6-(3,5,5-trimethylcyclohexen-1-yl)phenol as a thick yellowish oil (compound (106), Table 1).

g) The preparation of compound (107), Table 1, is disclosed in EP-A-0 705 870, Example 2.

h) The preparation of compound (108), Table 1, is disclosed in U.S. Pat. No. 5,414,033, Example 1.

i) Preparation of compound (109) (Table 1).

15.0 g (0.10 mol) of 4-tert-butylphenol and 7.2 g (0.035 mol) of aluminium isopropylate are added to 100 ml of xylene under nitrogen. To remove the resulting isopropanol, 30 ml of solvent are distilled off. The reaction mixture is heated to 100° C. and charged with 9.8 g (0.10 mol) of cyclohexanone and is then refluxed for 20 hours. The reaction mixture is cooled and charged with 40 ml of water and 10 ml of concentrated hydrochloric acid. The organic phase is separated, washed with water, dried over magnesium sulfate and concentrated on a rotary evaporator. The residue is chromatographed over silica gel using the solvent system hexane/ethyl acetate=19:1 and the pure fractions are crystallised from methanol, giving 6.3 g (27%) of 4-tert-butyl-2-cyclohexen-1-yl-phenol, m.p. 90–93° C. (compound (109), Table 1).

j) Preparation of compound (110) (Table 1).

A mixture consisting of 66.1 g (0.20 mol) of 2,4-bis(1-methyl-1-phenylethyl)phenol and 9.8 g (0.10 mol) of cyclohexanone is melted together and is then saturated, with stirring, with hydrochloric acid gas at 40–45° C. After 19 hours, another 9.8 g (0.10 mol) of cyclohexanone are added. The reaction mixture is saturated again with hydrochloric acid gas and is then stirred for 21 hours. The reaction mixture is diluted with petroleum ether and washed with water. The organic phase is dried over magnesium sulfate and concentrated on a rotary evaporator. The residue is chromatographed over silica gel using the solvent system hexane/ethyl acetate=39:1, giving 1.3 g (2%) of 2-cyclohexen-1-yl-4,6-bis(1-methyl-1-phenylethyl)phenol as a thick yellowish oil (compound (110), Table 1).

k) Preparation of compound (111) (Table 1).

A mixture consisting of 36.1 g (0.20 mol) of 3-tert-butyl-4-hydroxyanisol, 19.6 g (0.20 mol) of cyclohexanone and 10 ml of acetic acid is placed in a reactor and saturated, with stirring, with hydrochloric acid gas at room temperature. After standing for 64 hours at room temperature, the mixture is again saturated with hydrochloric acid gas and stirred for another 5 hours at 40° C. The reaction mixture is diluted with hexane and washed with water, sodium chloride solution and sodium hydrogencarbonate solution. The organic phase is dried over magnesium sulfate and concentrated on a rotary evaporator. The residue is chromatographed over silica gel using the solvent system ethyl acetate/hexane=1:49, giving 15.1 g (29%) of 2-tert-butyl-6-cyclohexen-1-yl-4-methoxyphenol as a yellowish thick oil, $^1$H—NMR (CDCl$_3$), δ(ppm): 3.75 (s, 3H, OCH$_3$), 5.87 (m, 1H, cyclohexenyl—H), (compound (111), Table 1).

TABLE 1

| No. | Compound | M.p. (°C.) | Yield |
|---|---|---|---|
| 101 | | 98–112° C./0.08 mbar (boiling point) | 21% |
| 102 | | 102–104 | 73% |
| 103 | | 135–139 | 47% |

TABLE 1-continued

| No. | Compound | M.p. (°C.) | Yield |
|---|---|---|---|
| 104 | 2-(3,6-dihydro-2H-thiopyran-4-yl)-4-tert-butyl-6-tert-butylphenol | 115–119 | 74% |
| 105 | 2-(cyclohept-1-en-1-yl)-4-tert-butyl-6-tert-butylphenol | 78–80 | 9% |
| 106 | 2-(3,5,5-trimethylcyclohex-1-en-1-yl)-4-tert-butyl-6-tert-butylphenol | oil | 43% |
| 107 | 2-(1-phenylethenyl)-4-tert-butyl-6-tert-butylphenol | oil | 68% |
| 108 | 2-(cyclohex-1-en-1-yl)-4-methyl-6-tert-butylphenol | oil | 53% |
| 109 | 2-(cyclohex-1-en-1-yl)-4-tert-butylphenol | 90–93 | 27% |

TABLE 1-continued

| No. | Compound | M.p. (°C.) | Yield |
|---|---|---|---|
| 110 | [structure: phenol with OH, 2-(1-methyl-1-phenylethyl), 4-(1-methyl-1-phenylethyl), 6-(cyclohexen-1-yl) substituents] | oil | 2% |
| 111 | [structure: 2-tert-butyl-4-methoxy-6-(cyclohexen-1-yl)phenol] | Oel | 43% |

EXAMPLE 2

Preparation of the Compounds of Formula IV (Table 2)

a) Preparation of compound (202) (Table 2).

A mixture consisting of 28.7 g (0.10 mol) of 2,4-di-tert-butyl-6-cyclohexen-1-yl-phenol (compound 102, Example 1b) and 17.5 ml (0.20 mol) of phosphorus trichloride is refluxed under nitrogen for 5 hours. Excess phosphorus trichloride is removed by distillation and the residue is then distilled under vacuum at 165–167° C./0.01 mbar, giving 30.8 g (88%) of 6,8-di-tert-butyl-10-chloro-2,3,4,10-tetrahydro-1 H-9-oxa-10-phosphaphenanthrene, a colourless thick liquid which slowly crystallises when standing; $^{31}P$—NMR (CDCl$_3$): δ=130.5 ppm (s); $^{1}H$—NMR (CDCl$_3$): δ(ppm): 1.34 (s, 9H, (CH$_3$)$_3$C—), 1.44 (s, 9H, (CH$_3$)$_3$C—), (compound (202), Table 2).

The compounds (201), (203), (204), (205), (206), (207), (208), (209), (210) and (211) (Table 2) are prepared in general analogy to the procedure of Example 2a starting from the phenols described in the Examples 1a, 1c, 1d, 1e, 1f, 1g, 1h, 1i, 1j and 1k with phosphorus trichloride.

TABLE 2

| No. | Compound | M.p. (°C.) |
|---|---|---|
| 201 | [structure: chlorophosphite fused bicyclic with (CH$_3$)$_3$C substituent and cyclopentane ring] | resin |
| 202 | [structure: chlorophosphite fused bicyclic with (CH$_3$)$_3$C and C(CH$_3$)$_3$ substituents and cyclohexane ring] | resin |
| 203 | [structure: chlorophosphite fused bicyclic with (CH$_3$)$_3$C and C(CH$_3$)$_3$ substituents and tetrahydropyran ring with O] | resin |
| 204 | [structure: chlorophosphite fused bicyclic with (CH$_3$)$_3$C and C(CH$_3$)$_3$ substituents and thiane ring with S] | resin |

TABLE 2-continued

| No. | Compound | M.p. (°C.) |
|---|---|---|
| 205 | (structure: chlorophosphorus heterocycle with tert-butyl groups and cycloheptane ring) | resin |
| 206 | (structure: chlorophosphorus heterocycle with tert-butyl groups and methylated cyclohexene) | resin |
| 207 | (structure: chlorophosphorus heterocycle with tert-butyl groups and phenyl-vinyl substituent) | resin |
| 208 | (structure: chlorophosphorus heterocycle with tert-butyl group, methyl, and cyclohexene) | resin |
| 209 | (structure: chlorophosphorus heterocycle with tert-butyl group and cyclohexene) | resin |
| 210 | (structure: chlorophosphorus heterocycle with two cumyl (C(CH₃)₂Ph) groups and cyclohexene) | resin |
| 211 | (structure: chlorophosphorus heterocycle with tert-butyl, OCH₃, and cyclohexene) | resin |

EXAMPLE 3

Preparation of the Compounds of Formula I (Table 3)

a) Preparation of compound (301) (Table 3).

A mixture consisting of 2.74 g (0.01 mol) of 2,4-di-tert-butyl-6-cyclopenten-1-yl-phenol (compound (101), Example 1a) and 2.7 ml (0.031 mol) of phosphorus trichloride is refluxed under nitrogen for 17 hours. The reaction mixture is then cooled to 100° C., diluted with 30 ml of toluene and carefully hydrolysed with 20 ml of water over 10 minutes at 100° C. The organic phase is separated, washed with water, dried over sodium sulfate and concentrated on a rotary evaporator. Crystallisation of the residue from petroleum ether/toluene gives 1.6 g (50%) of compound (301), Table 3, m.p. 172–174° C. Analysis: calculated: C 71.67; H 8.55%, found: C 71.64; H 8.71%.

b) Preparation of compound (302) (Table 3).

A mixture consisting of 114.4 g (0.40 mol) of 2,4-di-tert-butyl-6-cyclohexen-1-yl-phenol (compound 102), Example 1b) and 52.5 ml (0.60 mol) of phosphorus trichloride is refluxed under nitrogen for 4 hours. The reaction mixture is then cooled to 100° C., carefully hydrolysed with 100 ml of water, stirred for 10 minutes at 100° C. and cooled to 0° C. The precipitated product is collected by filtration, washed with water until neutral and dried under vacuum at 60° C. Crystallisation from petroleum ether gives 119 g (90%) of compound (302), Table 3, m.p. 164–166° C. Analysis: calculated: C 72.26; H 8.79%, found: C 72.31; H 8.78%.

c) Preparation of compound (303) (Table 3).

A mixture consisting of 5.8 g (0.02 mol) of 2,4-di-tert-butyl-6-(3,6-dihydro-2H-pyran-4-yl)-phenol (compound (103), Example 1c) and 5.2 ml (0.06 mol) of phosphorus trichloride is refluxed under nitrogen for 23 hours. The reaction mixture is then cooled to 100° C., diluted with 50 ml of petroleum ether and carefully charged with 20 ml of water and hydrolysed for 15 minutes at 100° C. The reaction mixture is cooled and diluted with ethyl acetate. The organic phase is washed with water, dried over sodium sulfate and concentrated on a rotary evaporator. Crystallisation of the residue from petroleum ether gives 5.6 g (84%) of compound (303), Table 3, m.p. 156–157° C. Analysis: calculated: C 68.25; H 8.14%, found: C 68.24; H 8.06%.

d) Preparation of compound (304) (Table 3).

A mixture consisting of 6.1 g (0.02 mol) of 2,4-di-tert-butyl-6-(3,6-dihydro-2H-thiopyran-4-yl)-phenol (compound (104), Example 1d) and 2.6 ml (0.03 mol) of phosphorus trichloride is refluxed under nitrogen for 14.5 hours. The reaction mixture is then cooled to 100° C., diluted with 50 ml of petroleum ether and carefully charged with 20 ml of water and hydrolysed for 15 minutes at 100° C. The reaction mixture is cooled. The organic phase is washed with water, dried over sodium sulfate and concentrated on a rotary evaporator. Crystallisation of the residue from petroleum ether gives 6.5 g (93%) of compound (304), Table 3, m.p. 177–179° C. Analysis: calculated: C 65.12; H 7.77; S 9.15%, found: C 65.11; H 7.72; S 9.14%.

e) Preparation of compound (305) (Table 3).

A mixture consisting of 3.0 g (0.01 mol) of 2,4-di-tert-butyl-6-cyclohepten-1-yl-phenol (compound (105), Example 1e) and 2.6 ml (0.03 mol) of phosphorus trichloride is refluxed under nitrogen for 22 hours. The reaction mixture is then cooled to 100° C., diluted with 20 ml of toluene and carefully charged with 20 ml of water and hydrolysed for 15 minutes at 100° C. The organic phase is washed with water, dried over sodium sulfate and concentrated on a rotary evaporator. Crystallisation of the residue from hexane gives 2.8 g (81%) of compound (305), Table 3, m.p. 148–150° C. Analysis: calculated: C 72.80; H 9.02%, found: C 72.80; H 8.93%.

f) Preparation of compound (306) (Table 3).

A mixture consisting of 5.1 g (0.0155 mol) of 2,4-di-tert-butyl-6-(3,5,5-trimethylcyclohexen-1-yl)phenol (compound (106), Example 1f) and 4.2 ml (0.048 mol) of phosphorus trichloride is refluxed under nitrogen for 23.5 hours. The reaction mixture is then cooled to 100° C., diluted with 20 ml of toluene and carefully charged with 10 ml of water and hydrolysed for 15 minutes at 100° C. The organic phase is washed with water, dried over sodium sulfate and concentrated on a rotary evaporator. The residue is chromatographed over silica gel using the solvent system ethyl acetate/hexane=1:2, giving 4.55 g (78%) of compound (306), Table 3, as a colourless thick resin. Analysis: calculated: C 73.76; H 9.42%, found: C 73.74; H 9.38%.

g) Preparation of compound (307) (Table 3).

A mixture consisting of 5.25 g (0.017 mol) of di-tert-butyl-6-(1-phenylvinyl)phenol (compound (107), Example 1g) and 3 ml (0.034 mol) of phosphorus trichloride is refluxed under nitrogen for 15 hours. The reaction mixture is then cooled to 100° C., diluted with 50 ml of toluene and carefully charged with 15 ml of water and hydrolysed for 15 minutes at 100° C. The organic phase is washed with water, dried over sodium sulfate and concentrated on a rotary evaporator. Crystallisation of the residue from petroleum ether gives 2.05 g (34%) of compound (307), Table 3, m.p. 113° C. Analysis: calculated: C 74.55; H 7.68%, found: C 74.72; H 7.68%.

h) Preparation of compound (308) (Table 3).

A mixture consisting of 14.3 g (0.059 mol) of 2-tert-butyl-6-cyclohexen-1-yl-4-methylphenol (compound (108), Example 1h) and 10 ml (0.11 mol) of phosphorus trichloride is refluxed under nitrogen for 16 hours. The reaction mixture is then poured into 700 ml of water and extracted with 200 ml of ethyl acetate. The organic phase is washed with water, dried over sodium sulfate and concentrated on a rotary evaporator. Crystallisation of the residue from petroleum ether gives 14.0 g (82%) of compound (308), Table 3, m.p. 157–159° C. Analysis: calculated: C 70.33; H 7.98%, found: C 70.36; H 7.93%.

i) Preparation of compound (309) (Table 3).

A mixture consisting of 2.3 g (0.01 mol) of 4-tert-butyl-2-cyclohexen-1-yl-phenol (compound (109), Example 1i) and 2.7 ml (0.03 mol) of phosphorus trichloride is refluxed under nitrogen for 22 hours. The reaction mixture is then cooled to 100° C., diluted with 20 ml of toluene and carefully charged with 10 ml of water and hydrolysed for 10 minutes at 100° C. The organic phase is washed with water, dried over sodium sulfate and concentrated on a rotary evaporator. The residue is chromatographed over silica gel using ethyl acetate, giving 1.3 g (47%) of compound (309), Table 3, an amorphous resin. Mass spectrum for $C_{16}H_{21}O_2P$ (MG=276.3): $M^+$=276.

j) Preparation of compound (310) (Table 3).

A mixture consisting of 1.1 g (2.70 mmol) of 2-cyclohexen-1-yl-4,6-bis(1-methyl-1-phenylethyl)phenol (compound (110), Example 1j), 1 ml (11.0 mmol) of phosphorus trichloride and 1 ml of toluene is refluxed under nitrogen for 22 hours. The reaction mixture is then cooled to 100° C., diluted with 10 ml of toluene and carefully charged with 10 ml of water and hydrolysed for 30 minutes at 100° C. The organic phase is washed with water, dried over sodium sulfate and concentrated on a rotary evaporator. The residue is chromatographed over silica gel using the solvent system ethyl acetate/hexane=3:4, giving 0.2 g (16%) of compound (310), Table 3, an amorphous resin. Mass spectrum for $C_{30}H_{33}O_2P$ (MG=456.6): $M^+$=456.

k) Preparation of compound (311) (Table 3).

A mixture consisting of 10.4 g (0.04 mol) of 2-tert-butyl-6-cyclohexen-1-yl-4-methoxyphenol and 5.25 ml (0.06 mol) of phosphorus trichloride is refluxed under nitrogen for 4.5 hours. The reaction mixture is then diluted with 20 ml of ligroin (b.p. 80–110° C.) and carefully charged with 10 ml of water and hydrolysed for 10 minutes at reflux. The reaction mixture is cooled and the precipitated product is collected by filtration and washed with water and ligroin. Crystallisation of the filter residue from ligroin (b.p. 110–140° C.) affords 7.5 g (61%) of compound (311), Table 3, m.p. 123–126° C. Mass spectrum for $C_{17}H_{23}O_3P$ (MG=306.3): $M^+$=306.

TABLE 3

| No. | Compound | m.p. (°C.) | Yield |
|---|---|---|---|
| 301 | (structure shown) | 172–174 | 50% |

TABLE 3-continued

| No. | Compound | m.p. (°C.) | Yield |
|---|---|---|---|
| 302 | (structure: phosphorus heterocycle with (CH₃)₃C and C(CH₃)₃ substituents, cyclohexene fused) | 164–166 | 90% |
| 303 | (structure with (CH₃)₃C, C(CH₃)₃, and oxygen-containing ring) | 156–157 | 84% |
| 304 | (structure with (CH₃)₃C, C(CH₃)₃, and sulfur-containing ring) | 177–179 | 93% |
| 305 | (structure with (CH₃)₃C, C(CH₃)₃, cycloheptene fused) | 148–150 | 81% |
| 306 | (structure with (CH₃)₃C, C(CH₃)₃, and trimethyl-substituted cyclohexene) | resin | 78% |
| 307 | (structure with (CH₃)₃C, C(CH₃)₃, phenyl-substituted) | 113 | 34% |
| 308 | (structure with (CH₃)₃C, CH₃, cyclohexene fused) | 157–159 | 98% |
| 309 | (structure with C(CH₃)₃, cyclohexene fused) | amorphous | 47% |
| 310 | (structure with two cumyl groups (H₃C)(H₃C)(phenyl)C–, cyclohexene fused) | amorphous | 16% |
| 311 | (structure with (CH₃)₃C, OCH₃, cyclohexene fused) | 123–126 | 61% |

EXAMPLE 4

Stabilising an ABS Injection Moulding Composition Against Yellowing.

3 kg of ABS copolymer (Ronfalin®TZ 220, of DSM) and 9 g (0.3%) of the compound of Table 3 are mixed in a 10 liter aluminium flask on a Rhönrad for 30 minutes. This mixture is then extruded in a Schwabenthan single-screw extruder at 220° C. The polymer string is then granulated. Using an injection moulding machine of the Engel EK type, 60×44×2 mm plates are moulded from the granulate so obtained at 230° C. and at a residence time of 2 minutes. The yellowness index (YI) of these plates is determined according to ASTM D 1925-70. Low YI values denote little discolouration, high YI values strong discolouration of the plates. The less discolouration, the more effective the stabiliser. The results are compiled in Table 4.

TABLE 4

| Example | Compound of Table 3 | Yellowness Index |
|---|---|---|
| 4a | — | 62 |
| 4b | 302 | 57 |

What is claimed is:

1. A compound of formula I

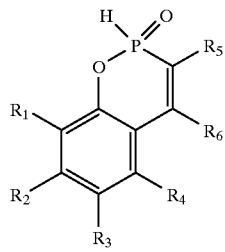

wherein $R_1$, $R_2$, $R_3$ and $R_4$ are each independently of one another hydrogen, halogen, hydroxy, $C_1$–$C_{25}$alkyl; $C_2$–$C_{25}$alkyl which is interrupted by oxygen, sulfur or

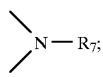

$C_2$–$C_{24}$alkenyl, $C_7$–$C_9$phenylalkyl, unsubstituted or $C_1$–$C_4$alkyl-substituted phenyl; unsubstituted or $C_1$–$C_4$alkyl-substituted $C_5$–$C_{12}$cycloalkyl; unsubstituted or $C_1$–$C_4$alkyl-substituted $C_5$–$C_{12}$cycloalkenyl; $C_1$–$C_{18}$alkoxy, $C_2$–$C_{24}$alkenyloxy, $C_1$–$C_{18}$alkylthio, $C_1$–$C_4$alkylamino, di($C_1$–$C_4$alkyl)amino, $C_1$–$C_{25}$alkanoyloxy, $C_1$–$C_{25}$alkanoylamino, $C_3$–$C_{25}$alkenoyloxy; $C_3$–$C_{25}$alkanoyloxy which is interrupted by oxygen, sulfur or

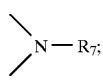

$C_5$–$C_9$cycloalkylcarbonyloxy, benzoyloxy or $C_1$–$C_{12}$alkyl-substituted benzoyloxy; or $R_1$ and $R_2$, or $R_2$ and $R_3$, or $R_3$ and $R_4$, together with the linking carbon atoms, form a benzene ring, $R_3$ additionally being —$(CH_2)_m$—$COR_8$ or —$(CH_2)_n OR_9$, or, if $R_2$ and $R_4$ are hydrogen, $R_3$ additionally being a radical of formula IIa, IIb or IIc

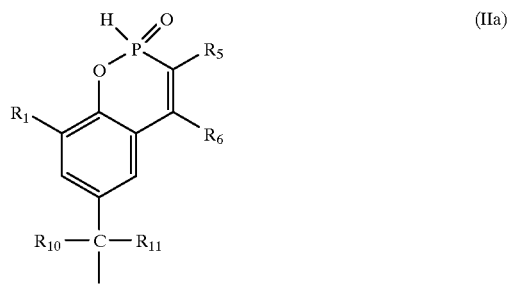

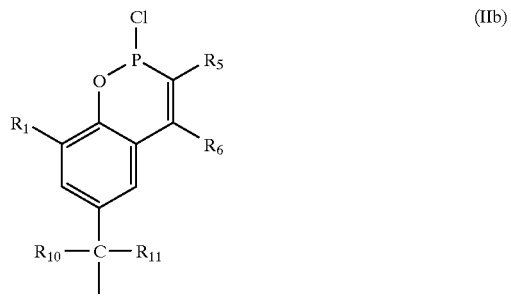

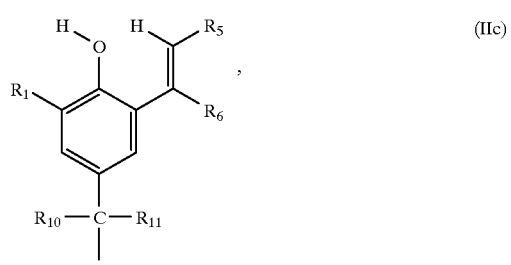

$R_5$ and $R_6$ are each independently of the other hydrogen, $C_1$–$C_{25}$alkyl; $C_2$–$C_{25}$alkyl which is interrupted by oxygen, sulfur or

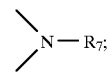

$C_7$–$C_9$phenylalkyl, unsubstituted or $C_1$–$C_4$alkyl-substituted phenyl; unsubstituted or $C_1$–$C_4$alkyl-substituted $C_5$–$C_{12}$cycloalkyl, or $R_5$ and $R_6$, together with the linking carbon atoms, are unsubstituted $C_5$–$C_{12}$cycloalkenylene or unsubstituted $C_4$–$C_{11}$cycloalkenylene which is interrupted by oxygen, sulfur or

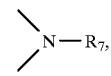

the rings of which are unsubstituted or substituted by $C_1$–$C_4$alkyl, by unsubstituted or $C_1$–$C_4$alkyl-substituted $C_5$–$C_{12}$cycloalkyl; by unsubstituted or $C_1$–$C_4$alkyl-substituted phenyl; or by unsubstituted or $C_1$–$C_4$alkyl-substituted phenylene, $R_7$ is hydrogen, $C_1$–$C_8$alkyl, $C_1$–$C_8$alkoxy, $C_1$–$C_8$alkanoyl or unsubstituted or $C_1$–$C_4$alkyl-substituted benzoyl, $R_8$ is hydroxy,

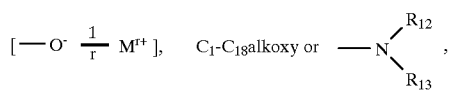

$R_9$ is hydrogen, $C_1$–$C_8$alkanoyl or unsubstituted or $C_1$–$C_4$alkyl-substituted benzoyl, $R_{10}$ and $R_{11}$ are each independently of the other hydrogen, $CF_3$, $C_1$–$C_{12}$alkyl, unsubstituted or $C_1$–$C_4$alkyl-substituted phenyl; or —(CH$_2$)$_s$—COR$_{14}$, or $R_{10}$ and $R_{11}$, together with the linking carbon atom, are a $C_5$–$C_{12}$cycloalkylidene ring which is unsubstituted or substituted by 1 to 3 $C_1$–$C_4$alkyl, $R_{12}$ and $R_{13}$ are each independently of the other hydrogen or $C_1$–$C_{18}$alkyl, $R_{14}$ is hydroxy, $C_1$–$C_{18}$alkoxy or

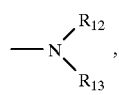

M is an r-valent metal cation,
m is 0, 1 or 2,
n is 1, 2, 3, 4, 5 or 6,
r is 1, 2 or 3, and
s is 0 or 1.

2. A compound according to claim 1, wherein $R_2$ and $R_4$ are hydrogen.

3. A compound according to claim 1, wherein
$R_5$ and $R_6$ are each independently of the other hydrogen, $C_1$–$C_4$alkyl or phenyl, or $R_5$ and $R_6$, together with the linking carbon atoms, are unsubstituted $C_5$–$C_7$cycloalkenylene or unsubstituted $C_5$–$C_6$cycloalkenylene which is interrupted by oxygen or sulfur, the rings of which are unsubstituted or substituted by $C_1$–$C_4$alkyl or phenyl.

4. A compound according to claim 1, wherein
$R_1$, $R_2$, $R_3$ and $R_4$ are each independently of one another hydrogen, chloro, hydroxy, $C_1$–$C_{18}$alkyl; $C_2$–$C_{18}$alkyl which is interrupted by oxygen, sulfur or

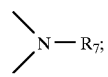

$C_2$–$C_{18}$alkenyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; unsubstituted or $C_1$–$C_4$alkyl-substituted $C_5$–$C_8$cycloalkenyl; $C_1$–$C_{18}$alkoxy, $C_2$–$C_{18}$alkenyloxy, $C_1$–$C_{18}$alkylthio, $C_1$–$C_4$alkylamino, di($C_1$–$C_4$alkyl)amino, $C_1$–$C_{18}$alkanoyloxy, $C_1$–$C_{18}$alkanoylamino, $C_3$–$C_{18}$alkenoyloxy; $C_3$–$C_{18}$alkanoyloxy which is interrupted by oxygen, sulfur or

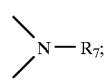

$C_5$–$C_9$cycloalkylcarbonyloxy, benzoyloxy or $C_1$–$C_4$alkyl-substituted benzoyloxy; or $R_1$ and $R_2$, or $R_2$ and $R_3$, or $R_3$ and $R_4$, together with the linking carbon atoms, form a benzene ring, $R_3$ additionally being —(CH$_2$)$_m$—COR$_8$ or —(CH$_2$)$_n$OR$_9$ or, if $R_2$ and $R_4$ are hydrogen, $R_3$ additionally being a radical of formula IIa

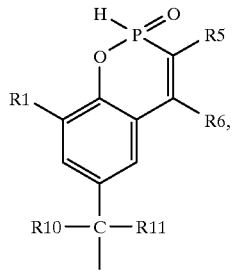

(IIa)

$R_5$ and $R_6$ are each independently of the other hydrogen, $C_1$–$C_{18}$alkyl; $C_2$–$C_{18}$alkyl which is interrupted by oxygen, sulfur or

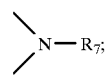

$C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl, or $R_5$ and $R_6$, together with the linking carbon atoms, are unsubstituted $C_5$–$C_9$cycloalkenylene or unsubstituted $C_4$–$C_8$cycloalkenylene which is interrupted by oxygen, sulfur or

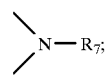

the rings of which are unsubstituted or substituted by $C_1$–$C_4$alkyl, by unsubstituted or $C_1$–$C_4$alkyl-substituted $C_5$–$C_8$cycloalkyl; by unsubstituted or $C_1$–$C_4$alkyl-substituted phenyl; or by phenylene, $R_7$ is hydrogen, $C_1$–$C_6$alkyl, $C_1$–$C_6$alkoxy, $C_1$–$C_6$alkanoyl or benzoyl, $R_8$ is hydroxy,

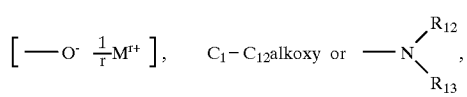

$R_9$ is hydrogen, $C_1$–$C_8$alkanoyl or benzoyl, $R_{10}$ and $R_{11}$ are each independently of the other hydrogen, $CF_3$, $C_1$–$C_{10}$alkyl, unsubstituted or $C_1$–$C_4$alkyl-substituted phenyl; or —(CH$_2$)$_s$—COR$_{14}$, or $R_{10}$ and $R_{11}$, together with the linking carbon atom, are a $C_5$–$C_9$cycloalkylidene ring which is unsubstituted or substituted by 1 to 3 $C_1$–$C_4$alkyl, $R_{12}$ and $R_{13}$ are each independently of the other hydrogen or $C_1$–$C_{12}$alkyl, $R_{14}$ is hydroxy, $C_1$–$C_{12}$alkoxy or

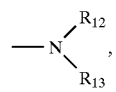

M is sodium, potassium, calcium or aluminium, m is 1 or 2, n is 2, 3, 4, 5 or 6, r is 1, 2 or 3, and s is 0 or 1.

5. A compound according to claim 1, wherein $R_1$, $R_2$, $R_3$ and $R_4$ are each independently of one another hydrogen, chloro, $C_1$–$C_{12}$alkyl, $C_2$–$C_{12}$alkyl which is interrupted by oxygen or sulfur; $C_2$–$C_{12}$alkenyl, $C_7$–$C_9$phenylalkyl, phenyl, $C_5$–$C_8$cycloalkyl, $C_5$–$C_8$cycloalkenyl, $C_1$–$C_{12}$alkoxy, $C_3$–$C_{12}$alkenyloxy, $C_1$–$C_{18}$alkylthio, $C_1$–$C_{12}$alkanoyloxy, $C_1$–$C_{12}$alkanoylamino, $C_3$–$C_{12}$alkenoyloxy; $C_3$–$C_{12}$alkanoyloxy which is interrupted by oxygen or sulfur; $C_5$–$C_8$cycloalkylcarbonyloxy or benzoyloxy; $R_3$ additionally being a radical of formula IIa

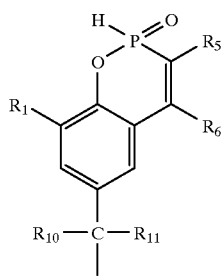

(IIa)

$R_5$ and $R_6$ are each independently of the other hydrogen, $C_1$–$C_{12}$alkyl; $C_2$–$C_{12}$alkyl which is interrupted by oxygen or sulfur; $C_7$–$C_9$phenylalkyl, phenyl or $C_5$–$C_8$cycloalkyl, or $R_5$ and $R_6$, together with the linking carbon atom, are unsubstituted $C_5$–$C_9$cycloalkenylene or $C_4$–$C_8$cycloalkenylene which is interrupted by oxygen or sulfur, the rings of which are unsubstituted or substituted by $C_1$–$C_4$alkyl, $C_5$–$C_{11}$cycloalkyl or phenyl, $R_{10}$ and $R_{11}$ are each independently of the other hydrogen, $CF_3$, $C_1$–$C_8$alkyl, phenyl or —$(CH_2)_s$—$COR_{14}$, or $R_{10}$ and $R_{11}$, together with the linking carbon atom, are a $C_5$–$C_9$cycloalkylidene ring, $R_{14}$ is hydroxy or $C_1$–$C_{12}$alkoxy, and s is 0 or 1.

6. A compound according to claim 1, wherein $R_1$ is hydrogen, $C_1$–$C_4$alkyl, cyclohexyl, 1-cyclohexenyl or $C_7$–$C_9$phenylalkyl, $R_2$ is hydrogen, $R_3$ is hydrogen, $C_1$–$C_4$alkyl, cyclohexyl, 2-cyclohexenyl, $C_7$–$C_9$phenylalkyl or $C_1$–$C_4$alkoxy, $R_4$ is hydrogen, and $R_5$ and $R_6$ are each independently of the other hydrogen, $C_1$–$C_4$alkyl or phenyl, or $R_5$ and $R_6$, together with the linking carbon atoms, are unsubstituted $C_5$–$C_7$cycloalkenylene or unsubstituted $C_5$–$C_6$cycloalkenylene which is interrupted by oxygen or sulfur, the rings of which are unsubstituted or substituted by $C_1$–$C_4$alkyl or phenyl.

7. A compound according to claim 1, wherein $R_1$ is hydrogen, $C_1$–$C_4$alkyl or $C_7$–$C_9$phenylalkyl, $R_2$ is hydrogen, $R_3$ is $C_1$–$C_4$alkyl, $C_7$–$C_9$phenylalkyl or $C_1$–$C_4$alkoxy, $R_4$ is hydrogen, and $R_5$ and $R_6$ are each independently of the other hydrogen or phenyl, or $R_5$ and $R_6$, together with the linking carbon atoms, are unsubstituted $C_5$–$C_7$cycloalkenylene or unsubstituted $C_5$cycloalkenylene which is interrupted by oxygen or sulfur, the rings of which are unsubstituted or substituted by $C_1$–$C_4$alkyl.

8. A composition, comprising a) an organic material which is subject to oxidative, thermal or light-induced degradation, and b) at least one compound of formula I as claimed in claim 1.

9. A composition according to claim 8, which comprises additional additives besides components (a) and (b).

10. A composition according to claim 9, wherein the additional additives are phenolic anti-oxidants, light stabilisers or/and processing stabilisers.

11. A composition according to claim 9, wherein the additional additive is at least one compound of the benzofuran-2-one type.

12. A composition according to claim 8, wherein component (a) is a natural, semi-synthetic or synthetic polymer.

13. A composition according to claim 8, wherein component (a) is a thermoplastic polymer.

14. A composition according to claim 8, wherein component (a) is a copolymer or graft copolymer of styrene or a-methylstyrene with dienes, polybutadiene or acrylic derivatives.

15. A composition according to claim 8, wherein component (a) is an ABS injection moulding composition.

16. A composition according to claim 8, wherein component (b) is present in an amount of 0.01 to 10%, based on the weight of component (a).

17. A process for stabilising an organic material against oxidative, thermal or light-induced degradation, which comprises incorporating in, or applying to, said material at least one compound of formula I as claimed in claim 1.

18. A process for the preparation of a compound of formula I

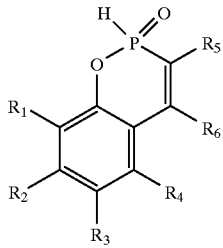

(I)

wherein the general symbols are as defined in claim 1, which process comprises reacting a compound of formula III

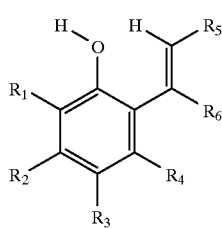
(III)
wherein the general symbols are as defined in claim 1, with phosphorus trichloride to a compound of formula IV
(IV)
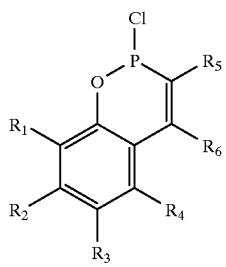
wherein the general symbols are as defined in claim 1, and subsequently hydrolysing this compound with water without isolation.
19. A compound of formula IV
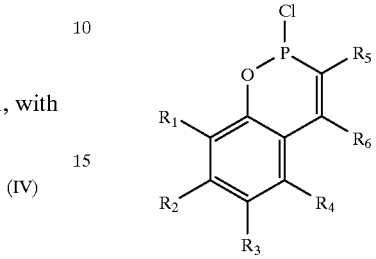
(IV)
wherein the general symbols are as defined in claim 1.
* * * * *